(12) United States Patent
Zuppiger

(10) Patent No.: US 8,435,464 B2
(45) Date of Patent: May 7, 2013

(54) SYSTEM AND METHOD FOR PIPETTING OF FLUIDS, METHOD FOR CALIBRATING THE SYSTEM

(75) Inventor: Adelrich Zuppiger, Siebnen (CH)

(73) Assignee: Roche Diagnostics Operations, Inc., Indianapolis, IN (US)

(*) Notice: Subject to any disclaimer, the term of this patent is extended or adjusted under 35 U.S.C. 154(b) by 216 days.

(21) Appl. No.: 12/770,863

(22) Filed: Apr. 30, 2010

(65) Prior Publication Data

US 2011/0111506 A1 May 12, 2011

(30) Foreign Application Priority Data

Apr. 30, 2009 (EP) .................................. 09159200

(51) Int. Cl.
*B01L 3/02* (2006.01)
(52) U.S. Cl.
USPC ............ 422/522; 422/521; 422/501; 436/180
(58) Field of Classification Search .......................... None
See application file for complete search history.

(56) References Cited

U.S. PATENT DOCUMENTS

| 5,423,661 | A | 6/1995 | Gabeler et al. |
| 6,589,791 | B1 | 7/2003 | LaBudde et al. |
| 2005/0074360 | A1* | 4/2005 | DeWalch .................. 422/63 |
| 2006/0211132 | A1 | 9/2006 | Miledi et al. |
| 2007/0025882 | A1 | 2/2007 | Zuppiger et al. |
| 2007/0177986 | A1 | 8/2007 | Leibfried |

FOREIGN PATENT DOCUMENTS

| EP | 1 391 611 A2 | 2/2004 |
| WO | 83/04015 | 11/1983 |
| WO | 98/35761 | 8/1998 |

* cited by examiner

*Primary Examiner* — Yelena G Gakh
*Assistant Examiner* — Christopher A Hixson
(74) *Attorney, Agent, or Firm* — Dinsmore & Shohl LLP

(57) ABSTRACT

A system and a method for the automated pipetting of fluids are disclosed as well as a method for calibrating the system. A channel pump having at least one tip-sided port connected to a pipetting tip by a tip-sided pump conduit for generating a positive or negative pressure in the pipetting tip, and at least one reservoir-sided port connected to a system fluid reservoir by a reservoir-sided pump conduit is provided. The channel pump when operated at a nominal flow rate exhibits a fluid backflow caused by a pressure difference in the tip- and reservoir-sided pump conduits which results in an effective flow rate compared to the nominal flow rate. Such a pressure difference can be used to determine an extended pipetting period which extends a pipetting period of the channel pump operating at the nominal flow rate, and to calibrate the system.

14 Claims, 11 Drawing Sheets

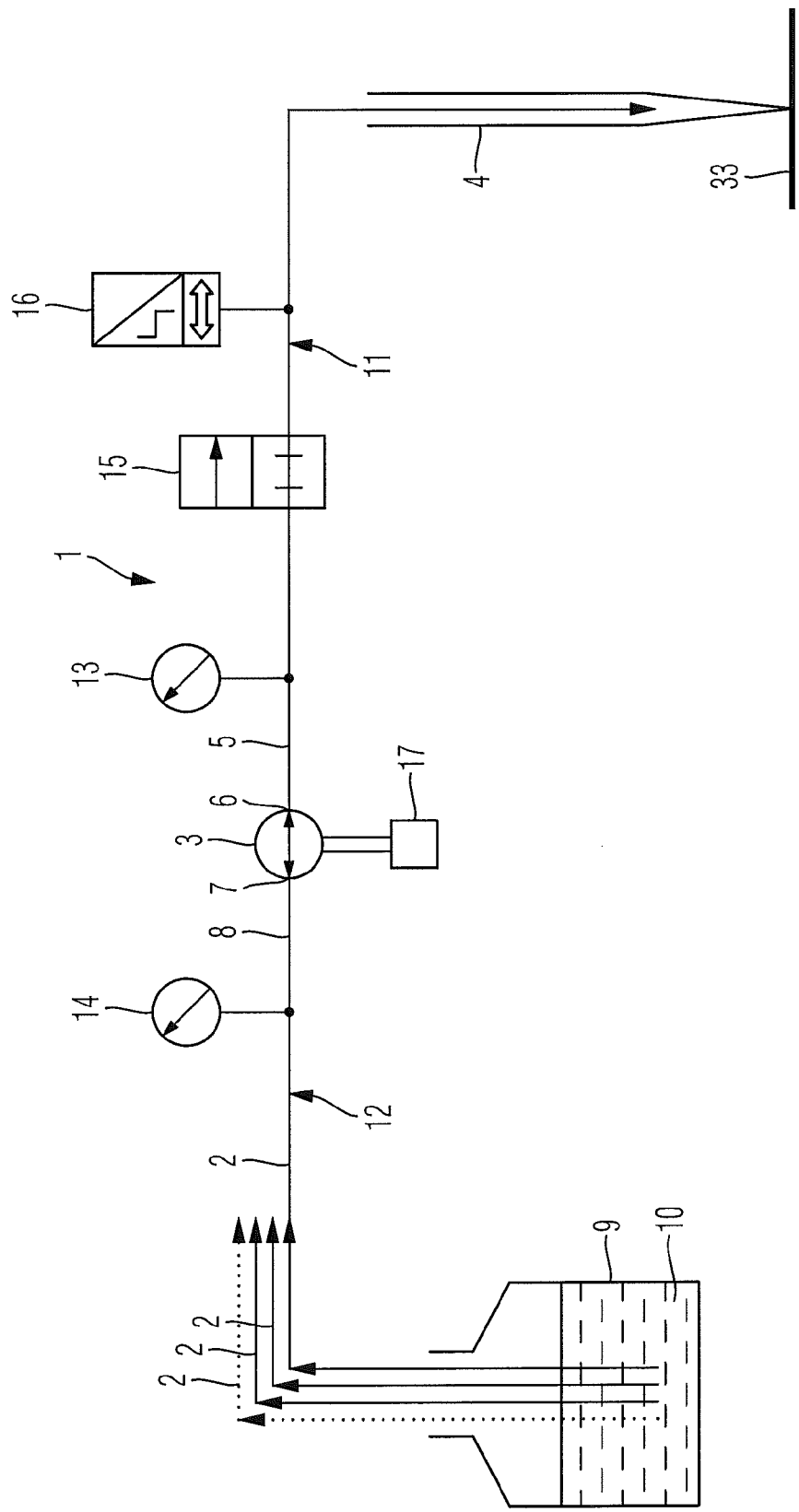

SYSTEM AND METHOD FOR PIPETTING OF FLUIDS, METHOD FOR CALIBRATING THE SYSTEM

TECHNICAL FIELD

Embodiments of the present invention disclosed herein are in the field of automated handling of fluids and in particular, various embodiments pertain to a system and a method for the automated pipetting of fluids. Other embodiments further relate to a method for calibrating the system.

BACKGROUND

In consideration of the fact that there is an ongoing increase in (bio-)chemical and genetic analyses and assays, a strong demand for the automated pipetting of fluids can be observed. For this reason, in recent years, many efforts have been made to develop new automated pipetting apparatus, e.g., enabling plural pipetting operations in parallel. Automated pipetting apparatus typically use plunger pumps which in order to enable precise pipetting of fluids have to be specifically sized to the intended range of pipetted fluid volumes. It is further known to use liquid system fluid which due to a reduced compressibility and lower temperature-induced variations compared to the otherwise purely gaseous system fluid improves preciseness of pipetting operations.

In order to avoid contamination of fluids, automated pipetting apparatus usually may be brought into a washing mode for performing washing operations, e.g., in-between consecutive pipetting operations. Due to the normally much greater fluid volumes required for washing operations compared to the pipetted fluid volumes, it is not appropriate to use plunger pumps for both pipetting and washing operations. In order to avoid such drawback, pumps other than plunger pumps which can be used for both pipetting and washing operations such as pumps of the rotary displacement pump type have been envisaged for use in automated pipetting apparatus.

SUMMARY

In light of the foregoing background, various embodiments of the invention provide an improved system and method for the pipetting of fluids which, while being flexible in use, allow for a highly precise pipetting of fluids.

According to an embodiment, a pipetting system is disclosed which comprises at least one pipetting channel for pipetting of fluids and includes a channel pump having at least one tip-sided port connected to a pipetting tip by a tip-sided pump conduit which generates a positive or negative pressure in the pipetting tip and at least one reservoir-sided port connected to a system fluid reservoir by a reservoir-sided pump conduit. The channel pump exhibits a fluid backflow caused by a pressure difference in the tip- and reservoir-sided pump conduits which results in an effective flow rate ($F_{eff}$) compared to a nominal flow rate ($F_{nom}$). A controller is provided which: determines a pressure difference ($\Delta p$) between the tip- and reservoir-sided pump conduits; based on the pressure difference ($\Delta p$), determines a volume difference ($\Delta V$) between a nominal volume ($V_{nom}$) and an effective volume ($V_{eff}$) pipetted by operating the channel pump during a pipetting period ($T_p$) at the nominal flow rate ($F_{nom}$), the effective volume ($V_{eff}$) being reduced compared to the nominal volume ($V_{nom}$) due to the fluid backflow; based on the determined volume difference ($\Delta V$), determines a period extension ($\Delta T$), the period extension ($\Delta T$) being adapted for pipetting of the volume difference ($\Delta V$); and pipettes fluid by operating the channel pump at the nominal flow rate ($F_{nom}$) during an extended pipetting period ($T_{tot}$) which extends the pipetting period ($T_p$) by the period extension ($\Delta T$).

In another embodiment, a method for pipetting of fluids is disclosed which comprises providing a pipetting system having at least one pipetting channel for pipetting of fluids, and includes a channel pump having at least one tip-sided port connected to a pipetting tip by a tip-sided pump conduit which generates a positive or negative pressure in the pipetting tip and at least one reservoir-sided port connected to a system fluid reservoir by a reservoir-sided pump conduit. The channel pump exhibits a fluid backflow caused by a pressure difference in the tip- and reservoir-sided pump conduits which results in an effective flow rate ($F_{eff}$) compared to a nominal flow rate ($F_{nom}$). The method further includes determining a pressure difference ($\Delta p$) in the tip- and reservoir-sided pump conduits; and based on the pressure difference ($\Delta p$), determining a volume difference ($\Delta V$) between a nominal volume ($V_{nom}$) and an effective volume ($V_{eff}$) pipetted by operating the channel pump during a pipetting period ($T_p$) at the nominal flow rate ($F_{nom}$), the effective volume ($V_{eff}$) being reduced compared to the nominal volume ($V_{nom}$) due to the fluid backflow. Based on the determined volume difference ($\Delta V$), the method also includes determining a period extension ($\Delta T$), the period extension ($\Delta T$) being adapted for pipetting the volume difference ($\Delta V$); and pipetting fluid by operating the channel pump at the nominal flow rate ($F_{nom}$) during an extended pipetting period ($T_{tot}$) which extends the pipetting period ($T_p$) by the period extension ($\Delta T$).

In still another embodiment, a method for calibrating a pipetting system is disclosed which comprises providing a pipetting system comprising at least one pipetting channel for pipetting of fluids and includes a channel pump having at least one tip-sided port connected to a pipetting tip by a tip-sided pump conduit which generates a positive or negative pressure in the pipetting tip and at least one reservoir-sided port connected to a system fluid reservoir by a reservoir-sided pump conduit. The channel pump exhibits a fluid backflow caused by a pressure difference ($\Delta p$) in the tip- and reservoir-sided pump conduits which results in an effective flow rate ($F_{eff}$) compared to a nominal flow rate ($F_{nom}$). The method further includes inhibiting fluid flow through the channel pump; operating the channel pump at at least one nominal flow rate ($F_{nom}$) and determining at least one pressure difference ($\Delta p'$) in the tip-reservoir-sided pump conduits; determining at least one blocked-condition nominal flow rate ($F'_{nom}$) achieved by operating the channel pump and identifying the blocked-condition nominal flow rate ($F'_{nom}$) as fluid backflow rate ($F'_{back}$); and establishing a relationship between the determined pressure difference ($\Delta p'$) and the fluid backflow rate ($F'_{back}$).

Other and further features and advantages of these and other embodiments of the invention will appear more fully from the following detailed description and the accompanying drawings.

BRIEF DESCRIPTION OF THE DRAWINGS

FIG. 1 depicts a schematic diagram of an exemplary embodiment of a pipetting system according to the invention;

REFERENCE LIST

Figure 2A:
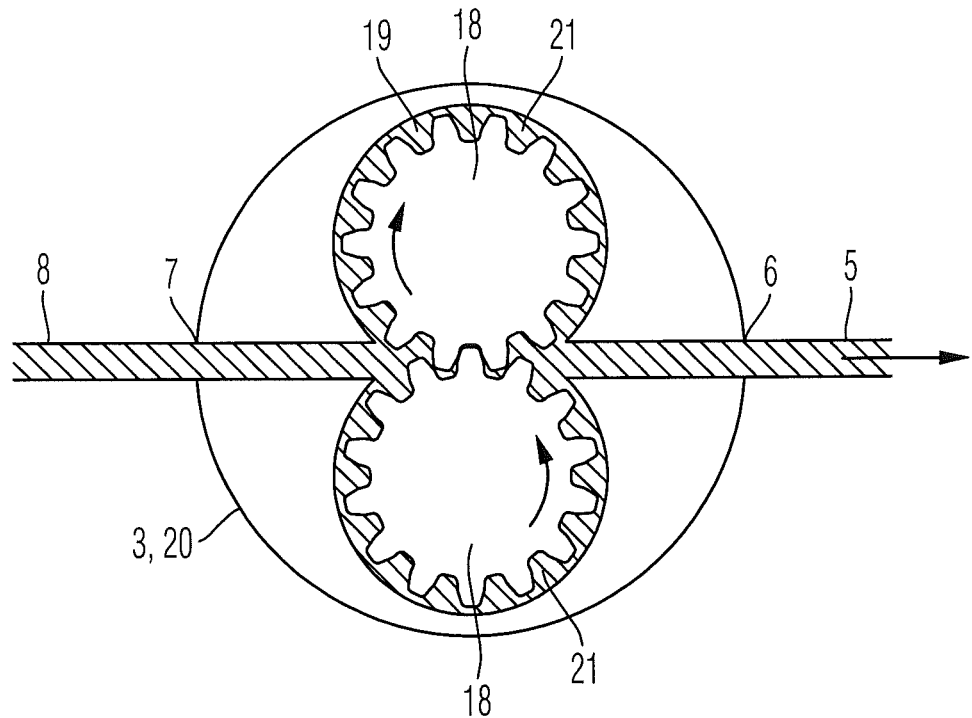
FIGS. 2A-2B depict schematic cross-sectional views illustrating a micro-gearwheel pump of the pipetting system of FIG. 1.

1 System
2 Pipetting channel
3 Micro-gearwheel pump
4 Pipetting tip
5 Tip tubing
6 Tip-sided port
7 Reservoir-sided port
8 Reservoir tubing
9 System fluid reservoir
10 System fluid
11 Tip-sided sub-channel
12 Reservoir-sided sub-channel
13 Tip-sided pressure sensor
14 Reservoir-sided pressure sensor
15 Fluid valve
16 Sensor arrangement
17 Controller
18 Gearwheel
19 Cavity
20 Pump housing
21 Pressure chamber
22 Inner wall
23 Outer wall
24 Gap
25 Nominal flow rate
26 Fluid backflow rate
27 Upper curve
28 Lower curve
29 Effective flow rate
30 Positioning device
31 Tube
32 Orifice
33 Tip blocker
34 Intermediate reservoir
35 Fluid surface
36 Surface
37 Work-plate
38 Fluid level sensor
39 Housing
40 UV-Lamp
41 Reservoir tubing
42 Reservoir pump
43 Inlet port
44 Outlet port
45 Reservoir sensor arrangement

DETAILED DESCRIPTION

According to an embodiment of the invention, a new system for the automated pipetting of fluids is disclosed. The pipetting system comprises at least one (e.g. modular) pipetting channel for pipetting of fluids provided with a first pump, which in the following is denoted as a "channel pump", having at least one tip-sided port fluidically connected to a pipetting tip by means of a tip-sided pump conduit and at least one reservoir-sided port fluidically connected to a first fluid reservoir, which in the following is denoted as a "system fluid reservoir", by means of a reservoir-sided pump conduit.

In one embodiment, the channel pump can be operated at a nominal flow rate for generating a positive or negative pressure in the pipetting tip for aspirating or dispensing of fluid through the pipetting tip. The nominal flow rate is a flow rate that is achieved for zero pressure difference between the tip-sided pump and the reservoir-sided pump conduit. In case of a pump of the rotary displacement pump type, the nominal flow rate depends on a rotational speed of a rotary displacement body of the pump. It usually is indicated by manufacturers and can be readily determined by measuring the number of revolutions per time unit (i.e. rotational speed) of the rotary displacement body, e.g., by means of a rotary encoder adapted to convert a rotary position of the rotary displacement body to an analogue or digital electronic signal. In another embodiment, the channel pump can be operated at plural nominal flow rates different with respect to each other.

The channel pump exhibits a leakage-caused fluid backflow when operated at one nominal flow rate caused by different fluid pressures in the pump conduits on the delivery and suction sides of the channel pump. Due to the normally positive pressure difference between the tip-sided pump conduit and the reservoir-sided pump conduit, the fluid backflow is oppositely directed to the pump-generated fluid flow to reduce the nominal flow rate to an effective flow rate. Hence, the effective flow rate is the nominal flow rate reduced by a flow rate due to the leakage-caused fluid backflow.

Accordingly, due to the reduced (effective) flow rate achieved when the channel pump is operated at the nominal flow rate, an effective volume pipetted during a predetermined pipetting period is reduced compared to a nominal volume as derived from the nominal flow rate.

The fluid backflow exhibiting channel pump used in the pipetting system embodiment may, e.g., be embodied as pump of the rotary displacement pump type such as a micro-gearwheel pump. While being comparably low in weight, micro-gearwheel pumps advantageously allow for highly-precise pipetting of fluids and enable pipetting operations in a wide range of flow rates enabling a same pump to be used for both pipetting and washing operations.

The pipetting system according to another embodiment of the invention further includes a controller for control of pipetting operations for the automated pipetting of fluids. The controller may, e.g., be embodied as programmable logic controller running a machine-readable program provided with instructions to perform pipetting of fluids.

In an embodiment of the pipetting system, the controller is set up to control the following processes. A process of determining a pressure difference between a fluid pressure in the tip-sided pump conduit and a fluid pressure in the reservoir-sided pump conduit arising when the channel pump is operated at the nominal flow rate. Based on the above-determined pressure difference, a process of determining a volume difference between a nominal volume and a reduced (effective) volume pipetted when the channel pump is operated during a predetermined pipetting period at the nominal flow rate. According to the above, the pipetted effective volume is reduced compared to the nominal volume due to the leakage-caused fluid backflow of the channel pump. Based on the above-determined volume difference, a process of determining a time span, in the following denoted as "period extension," adapted for pipetting of the above-determined volume difference when the channel pump is operated at the nominal flow rate during the period extension. Based on the above-determined period extension, a process of operating the channel pump at the nominal flow rate resulting in the backflow-reduced effective flow rate during an extended pipetting period composed of the pipetting period and the period extension.

Accordingly, based on determining a pressure difference between fluid pressures in the pump conduits downstream and upstream the channel pump, a leakage-caused fluid backflow can be readily compensated by prolonging the pipetting period by the period extension to thereby enable highly-precise pipetting operations.

According to another embodiment of the pipetting system, the pipetting system includes a first fluid pressure sensor which senses a fluid pressure in the tip-sided pump conduit fluidically connecting the channel pump and the pipetting tip. In this embodiment, the controller measures a fluid pressure in the tip-sided pump conduit after starting the pipetting operation for pipetting of fluid.

In above embodiment, in order to determine the pressure difference between fluid pressures in the tip-sided pump conduit and the reservoir-side pump conduit, the controller in one embodiment determines a fluid pressure in the reservoir-sided pump conduit by means of a calculation model which may be based on a set of parameters describing the pump and the reservoir-sided pump conduit and another set of parameters describing the fluid contained in the reservoir-sided pump conduit. Alternatively, the controller sets the fluid pressure in the reservoir-sided pump conduit to have a predetermined constant value. Yet alternatively, the pipetting system may include a second fluid pressure sensor which senses a fluid pressure in the reservoir-sided pump conduit, wherein the controller measures a fluid pressure in the reservoir-sided pump conduit after starting the pipetting operation. Yet alternatively, the pipetting system may include an air pressure sensor which senses ambient air pressure, wherein the controller measures an ambient air pressure identified as fluid pressure in the reservoir-sided pump conduit.

According to another embodiment of the pipetting system, the controller determines plural fluid pressures at different times in both the tip-sided pump conduit and the reservoir-sided pump conduit to determine a plurality of pressure differences to further enhance precision of pipetting operations. Particularly, a mean pressure difference such as an arithmetic means may be derived from the plural pressure differences to be used by the controller for determining the extended pipetting period.

According to yet another embodiment of the pipetting system, the system includes a fluid flow inhibiting device arranged downstream the channel pump and which inhibits fluid flow through the channel pump in order to calibrate the pipetting system. The fluid flow inhibiting device may, e.g., be embodied as tip blocker which externally blocks the pipetting tip so that fluid may not be dispensed or aspirated through the pipetting tip. Alternatively, the fluid flow inhibiting device may be embodied as fluid valve, e.g., arranged downstream the channel pump, e.g., in the tip-sided pump conduit, which can be brought in at least two different valve positions including fully open and fully closed positions which enable/inhibit fluid flow through the channel pump. In that embodiment, the pipetting system further includes a fluid pressure sensor which senses fluid pressure in the tip-sided pump conduit. It may further include an air pressure sensor which senses an ambient air pressure and may include another fluid pressure sensor which senses fluid pressure in the reservoir-sided pump conduit. It may yet further include a temperature sensor which senses fluid temperature in the pipetting channel.

In another embodiment, the controller performs the following processes. An initial process of inhibiting fluid flow through the channel pump by means of the fluid flow inhibiting device which, e.g., can be performed by placing the pipetting tip onto the tip blocker or closing the fluid valve as-above detailed.

Another process of operating the channel pump at one nominal flow rate and determining a pressure difference between fluid pressures in the tip-sided pump conduit and the reservoir-sided pump conduit. The determination of the pressure difference is based on measuring a fluid pressure in the tip-sided pump conduit by means of the fluid pressure sensor. It is further based on determining a fluid pressure in the reservoir-sided pump conduit either by using a calculation model as-above described, or alternatively, by setting the fluid pressure in the reservoir-sided pump conduit to have a predetermined constant value, or yet alternatively, by measuring an ambient air pressure by means of the air pressure sensor which then is identified as fluid pressure in the reservoir-sided pump conduit, or yet alternatively, by measuring a fluid pressure in the reservoir-sided pump conduit by means of the pressure sensor.

Another process of determining a blocked-condition nominal flow rate that is achieved when the channel pump is operated at the nominal flow rate pumping against the blocked pipetting channel by a flow rate determination means. In case of a channel pump of the rotary displacement pump type, the flow rate can, e.g., be determined based on sensing a rotational speed of the rotary displacement body by means of a rotational speed sensor such as a rotary encoder. The blocked-condition nominal flow rate achieved in pumping against the blocked pipetting channel is identified as fluid backflow rate. In other words, the fluid backflow rate equals the blocked-condition nominal pumping flow rate.

The above processes of determining a pressure difference between fluid pressures in the tip-sided pump conduit and the reservoir-sided pump conduit and determining the blocked-condition nominal flow rate may be repeated by operating the channel pump at plural nominal pumping flow rates which are different with respect to each other.

Based on the above, another process of establishing a (e.g. linear) relationship between the pressure difference (s) and the fluid backflow rate(s). In case of determining plural pressure differences and plural fluid backflow rates, such relationship can be established based on these plural values. In case of determining only one pressure difference and only one fluid backflow rate, a linear relationship can be readily established by identifying the determined fluid backflow rate as maximum fluid backflow rate occurring in case of maximum pressure difference and defining a minimum, e.g. zero, fluid backflow rate occurring in case of a predefined minimum, e.g. zero, pressure difference to thereby obtain a pair of pressure differences and a pair of fluid backflow rates.

Hence, a relationship between pressure differences and fluid backflow rates may be readily obtained to be used for determining the volume differences between nominal and reduced (effective) volumes pipetted at different pressure differences.

According to yet another embodiment of the pipetting system, the controller is set up to determine the pressure difference between fluid pressures in the tip-sided pump conduit and the reservoir-sided pump conduit based on an expected fluid pressure in the tip-sided pump conduit and an expected fluid pressure in the reservoir-sided pump conduit by means of a calculation model. In that case, the period extension may also be determined prior to starting the pipetting operation.

According to yet another embodiment of the pipetting system, the system includes a temperature sensor adapted for sensing a fluid temperature downstream and/or upstream the channel pump. In that case, the controller is configured to measure a fluid temperature in the pipetting channel to thereby enable a temperature-dependent determination of the pressure difference between fluid pressures in the tip-sided pump conduit and the reservoir-sided pump conduit in order to further improve precision of pipetting operations.

According to yet another embodiment of the pipetting system, the system includes at least one second fluid reservoir, in the following denoted as "intermediate reservoir" fluidically inter-connected between the system fluid reservoir and the channel pump for transferring fluid from the system fluid reservoir to the inter-mediate reservoir. Advantageously, the intermediate fluid reservoir has an invariant fluid level with respect to the channel pump. By this measure, preciseness of pipetting operations can advantageously be enhanced. Stated more particularly, due to an invariant hydrostatic pressure in the tip-sided pump conduit, hydrostatic pressure variances resulting from varying fluid levels in the intermediate reservoir can advantageously be avoided resulting in a highly-constant fluid backflow of the channel pump to thereby enhance precision of pipetting operations.

In order to determine a fluid level in the intermediate reservoir, it may be preferred that the pipetting system includes a fluid level sensor adapted for sensing a fluid level in the intermediate reservoir. Alternatively, the fluid level in the intermediate reservoir may be kept constant based on an ambient air pressure controlled re-fill mechanism similarly to a "bird bath". The system may further include a presence sensor adapted for sensing the presence of the intermediate reservoir.

According to yet another embodiment of the pipetting system, it further comprises a second pump, in the following denoted as "reservoir pump" which is fluidically interconnected between the system fluid reservoir and the intermediate reservoir. In that embodiment, the controller is set up to control a transfer of fluid from the system fluid reservoir to the intermediate reservoir so as to have an invariant fluid level in the intermediate reservoir with respect to the channel pump. The reservoir pump may be different from the channel pump and, e.g., may be embodied as pump of the membrane or plunger pump type. In one embodiment, the reservoir pump can be operated in only one single pumping direction to transfer fluid from the system fluid reservoir to the intermediate reservoir.

According to yet another embodiment of the pipetting system, it further comprises a positioning device for positioning the pipetting tip. In that embodiment, the controller is set up to control moving of the pipetting tip with respect to the invariant fluid level of the intermediate reservoir.

According to yet another embodiment of the pipetting system, it comprises a, e.g. closed, housing at least accommodating the intermediate reservoir which in this case may be considered an inner reservoir. The system fluid reservoir may be arranged outside the housing and, thus, maybe considered an outer reservoir. In that case, the outer reservoir may be readily manipulated even during an ongoing pipetting run, e.g., to be filled with fresh fluid or replaced by another system fluid reservoir.

According to yet another embodiment of the pipetting system, it comprises a plurality of system fluid reservoirs which, e.g., may be filled with different fluids. By this measure, separate fluid volumes may be used to transfer fluid to the intermediate reservoir to keep a larger volume of fluid ready for use with pipetting operations and to avoid early contamination with contaminants such as microbes. Otherwise, the fluid reservoirs may be filled with different fluids which can be mixed so that fluid contained in the intermediate reservoir can be mixed, changed or replaced.

According to yet another embodiment of the pipetting system, it further includes a microbe-reducing device adapted for reducing microbes in the intermediate reservoir such as a microbe filter or an ultraviolet light emitting lamp. Alternatively, the intermediate reservoir may be preserved by an antimicrobial agent.

In an embodiment of the pipetting system, fluid aspirated or dispensed through the pipetting tip may be similar to or different from fluid contained in the system fluid reservoir. Fluid contained in the system fluid reservoir may, e.g., be used as liquid system fluid for moving back and forth within the pipetting channel with or without a gas bubble in-between the pipetted fluid and the (non-pipetted) system fluid to enhance precision of pipetting operations. The system fluid may also be used for washing operations to wash the pipetting channel.

The channel pump used for pipetting fluids preferably, but not necessarily, may be operated in both pumping directions to aspirate or dispense fluid, and, may in particular be used for moving liquid system fluid back and forth within the pipetting channel.

The pipetting system may be part of a system for the automated processing of fluids which may be configured in various ways in accordance with specific demands as long as the processing of fluids involves automated pipetting of fluids. The system for the automated processing of fluids may, e.g., be embodied as analyzer for analyzing of fluids typically involving mixing of fluids with reagents to determine presence and optionally amount of specific substances contained in the fluids. It may also be embodied as pre-analytic preparator for the automated preparation of fluids prior to their analysis such as an extractor for the automated extraction of nucleic acids prior to their amplification.

Fluids to be automatically processed by such system may include biological fluids, e.g. blood, serum, urine, cerebrospinal fluids and nucleic acids, non-biological fluids, e.g. chemical compounds and drugs, and any other fluid of interest as long as automated processing thereof involves automated pipetting operations.

According to another embodiment of the invention, a new method for pipetting of fluids is disclosed. It comprises providing a pipetting system including at least one pipetting channel for pipetting fluids. The pipetting channel is provided with a first pump ("channel pump") having at least one tip-sided port connected to a pipetting tip by means of a tip-sided pump conduit for generating a positive or negative pressure in the pipetting tip and at least one reservoir-sided port connected to a fluid reservoir by means of a reservoir-sided pump conduit. The channel pump exhibits fluid backflow caused by a pressure difference between fluid pressures in the tip-sided pump conduit and the reservoir-sided pump conduit resulting in a reduced (effective) flow rate compared to a nominal flow rate. In that, a pipetting system according to any one of the various embodiments disclosed may be used for performing the method embodiments of the invention.

The method may further comprises determining a pressure difference between fluid pressures in the tip-sided pump conduit and the reservoir-sided pump conduit arising when a pipetting operation is performed.

Based on the above-determined pressure difference, the method may further comprise determining a volume difference between a nominal volume and a reduced (effective) volume pipetted when the channel pump is operated at the nominal flow rate during a pre-determined pipetting period. The effective volume is reduced compared to the nominal volume due to the fluid backflow of the channel pump.

Based on the above-determined volume difference, the method may further comprise determining a period extension adapted for pipetting of the above-determined volume difference when the channel pump is operated at the nominal flow rate during the period extension.

The method may further comprise performing a pipetting operation for pipetting fluid by operating the channel pump at the nominal flow rate during an extended pipetting period composed of the pipetting period and the period extension.

According to another embodiment, the method comprises measuring a fluid pressure in the tip-sided pump conduit arising during a pipetting operation, wherein the pressure difference is determined based on the measured fluid pressure in the tip-sided pump conduit. In this embodiment, in order to determine the pressure difference between fluid pressures in the tip- and reservoir-sided pump conduits, a fluid pressure in the reservoir-sided pump conduit may be determined by means of a calculation model. Alternatively, a fluid pressure in the reservoir-sided pump conduit may be determined by setting a fluid pressure in the reservoir-sided pump conduit to have a predetermined constant value. Yet alternatively, a fluid pressure in the reservoir-sided pump conduit may be determined in measuring an ambient air pressure which is taken as fluid pressure in the reservoir-sided pump conduit. Yet alternatively, a fluid pressure in the reservoir-sided pump conduit maybe measured by means of a fluid pressure sensor.

According to yet another embodiment, the method comprises determining a plurality of fluid pressure differences, wherein determination of the period extension is based on the plural fluid pressure differences.

According to yet another embodiment, the method comprises transferring fluid from the system fluid reservoir into an intermediate reservoir fluidically interconnected between the system fluid reservoir and the channel pump so as to have an invariant fluid level in the intermediate reservoir with respect to the channel pump.

According to yet another embodiment, the method comprises raising the pipetting tip so that an orifice of the pipetting tip has a vertical position higher than the fluid level of the intermediate reservoir during moving the pipetting tip towards or away from a pipetting position. By this measure, a negative hydrostatic pressure may be transferred to the pipetting tip to thereby reduce or even avoid dropping of fluid contained in the pipetting tip.

According to yet another embodiment, the method comprises lowering the pipetting tip so that an orifice of the pipetting tip has a vertical position lower than the fluid level of the intermediate reservoir during dispensing of fluid at the pipetting position.

According to another embodiment of the invention, a new method for calibrating a system for pipetting of fluids is disclosed. The method comprises providing a pipetting system which comprises at least one pipetting channel for pipetting fluids including a channel pump having at least one tip-sided port connected to a pipetting tip by means of a tip-sided pump conduit for generating a positive or negative pressure in the pipetting tip and at least one reservoir-sided port connected to a fluid reservoir by means of a reservoir-sided pump conduit. The channel pump exhibits a fluid backflow caused by a pressure difference between fluid pressures in the tip-sided pump conduit and the reservoir-sided pump conduit resulting in a reduced (effective) flow rate compared to a nominal flow rate. In that, the above-detailed pipetting system may, e.g., be used for performing the calibration method.

In another embodiment, the calibration method further comprises:

inhibiting fluid flow through the channel pump by means of a fluid flow inhibiting device which, e.g., can be performed in placing the pipetting tip onto the tip blocker or closing the fluid valve as-above detailed in connection with the system;

operating the channel pump at one nominal flow rate and determining a pressure difference between fluid pressures in the tip- and reservoir-sided pump conduit based on measuring a fluid pressure in the tip-sided pump conduit by means of a fluid pressure sensor adapted for measuring fluid pressure in the tip-sided pump conduit, wherein a fluid pressure in the reservoir-sided pump conduit can be determined by using a calculation model as-above described, or alternatively, by setting the fluid pressure in the reservoir-sided pump conduit to have a predetermined constant value, or yet alternatively, by measuring an ambient air pressure by means of the air pressure sensor which then is considered to be similar to the fluid pressure upstream the pump, or yet alternatively, by measuring a fluid pressure in the reservoir-sided pump conduit by means of the pressure sensor adapted for measuring fluid pressure in the tip-sided pump conduit;

determining a blocked-condition nominal flow rate when the channel pump is operated at the nominal flow rate pumping against the blocked pipetting channel by a flow rate determination means which, e.g., can be performed based on sensing a rotational speed of a rotary displacement body in a pump of the rotary displacement pump type by means of a rotational speed sensor such as a rotary encoder;

optionally repeating the determining a pressure difference between fluid pressures in the tip-sided pump conduit and the reservoir-sided pump conduit and the determining the blocked-condition nominal flow rate by operating the pump at plural nominal flow rates which are different with respect to each other;

establishing a (e.g. linear) relationship between the above-determined pressure difference(s) and the above-determined fluid backflow rate(s), wherein: (a) in case of determining plural pressure differences and plural fluid backflow rates, such relationship can be established based on these plural values; (b) in case of determining only one fluid pressure difference and only one fluid backflow rate, a linear relationship is established by identifying the fluid backflow rate as maximum fluid backflow rate occurring in case of maximum pressure difference and defining a minimum, e.g. zero, fluid backflow rate occurring in case of a predefined minimum, e.g. zero, pressure difference across the channel pump to thereby obtain a pair of pressure differences and a pair of backflow rates.

The above method for calibrating the pipetting system may, e.g., be performed in a periodic manner in which periods based on a predetermined number of pipetting operations or time intervals may be chosen. Alternatively, the calibration routine may, e.g., be performed each time the pipetting system is initialized. The method for calibrating the pipetting system may in particular be combined with above-described method for pipetting of fluids.

Various embodiments of the present invention will be described in detail below with reference to the accompanying drawings, where like designations denote like or similar elements.

Now referring to FIG. 1 an exemplary embodiment of the system 1 for the pipetting of fluids according to the invention is explained. The system 1 which, e.g., may be part of an automated analyzer for analyzing fluids includes a number of four (separate) pipetting channels 2 which are similar in construction. In FIG. 1, one single pipetting channel 2 is shown in detail for the purpose of illustration only. Each pipetting channel 2 may be considered a functional entity for the pipetting of fluids which, e.g., can be modular in construction. While the system 1 includes four pipetting channels 2, the system 1 may alternatively comprise a bigger or smaller number of pipetting channels 2 in accordance with specific demands for the pipetting of fluids.

Each pipetting channel 2 includes a bidirectional micro-gearwheel pump 3 having a tip-sided (inlet/outlet) port 6 fluidically connected to a pipetting tip 4 such as a metallic needle, e.g. made of steel, by means of flexible tip tubing 5 (in the introductory portion denoted as tip-sided pump conduit) for transferring a pump-generated positive or negative pressure to the pipetting tip 4. The tip tubing 5 is, e.g., made of plastic material. The pipetting tip 4 and at least a portion of the tip tubing 5 adjoining the pipetting tip 4 may mutually define a fluid duct for receiving fluids aspirated through the pipetting tip 4. The micro-gearwheel pump 3 is further provided with a reservoir-sided (inlet/outlet) port 7 fluidically connected to a system fluid reservoir 9 by means of flexible reservoir tubing 8 (in the introductory portion denoted as reservoir-sided pump conduit) for aspirating and dispensing, respectively, liquid system fluid 10 contained therein. Similar to the tip tubing 5, the reservoir tubing 8 is, e.g., made of plastic material.

As illustrated in FIG. 1, the system fluid reservoir 9 is filled with liquid system fluid 10. When performing a pipetting operation, the system fluid 10 is aspirated from or dispensed into the fluid reservoir 9 to thereby generate a negative or positive pressure in the pipetting tip 4 for aspirating or dispensing fluid through the pipetting tip 4. Regularly, a small gas bubble is kept in-between the system fluid 10 and fluid aspirated and dispensed through the pipetting tip 4 when performing a pipetting operation.

Stated more generally, each pipetting channel 2 is composed of the micro-gearwheel pump 3 connected to a tip-sided sub-channel 11 including the pipetting tip 4 connected to the micro-gearwheel pump 3 by the tip tubing 5 and a reservoir-sided sub-channel 12 including the fluid reservoir 9 connected to the micro-gearwheel pump 3 by the reservoir tubing 8. Due to the bidirectional operability of the micro-gearwheel pump 3 and depending on the actual pumping direction, each of the first and second sub-channels 11, 12 may serve as suction or delivery sides of the micro-gearwheel pump 3.

The pipetting channel 2 includes a tip-sided pressure sensor 13 arranged at the tip tubing 5 adapted for sensing of fluid pressure in the tip tubing 5. It further includes a reservoir-sided pressure sensor 14 arranged at the reservoir tubing 8 adapted for sensing a fluid pressure in the reservoir tubing 8. It yet further includes a sensor arrangement 16 arranged at the tip tubing 5 comprising plural sensors adapted for sensing various physical parameters, including an optical flow sensor adapted for sensing fluid flow in the tip tubing 5, a temperature sensor adapted for sensing fluid temperature in the tip tubing 5 and an air pressure sensor adapted for sensing ambient air pressure.

The tip tubing 5 passes through a fluid valve 15 adapted for opening or closing the tip tubing 5 to enable or inhibit fluid flow in the tip tubing 5 and micro-gearwheel pump 3, respectively.

In the pipetting system 1, each pipetting channel 2 may have shared components for sharing with other pipetting channels 2 such as the micro-gearwheel pump 3 or the fluid reservoir 9 and separate components not shared with other pipetting channels 2.

The pipetting system 1 further includes a controller 17 for controlling of pipetting of fluids which may be embodied as programmable logic controller running a computer-readable program provided with instructions to perform pipetting operations. In that, the controller 17 receives information from the different components of the pipetting system 1 and generates and transmits control signals for controlling these components. In that, the controller 17 is electrically connected to the system components which require control and/or provide information which include the micro-gearwheel pump 3, the fluid valve 15, the pressure sensors 13, 14 and the various sensors accommodated in the sensor arrangement 16. Specifically, the fluid valve 15 is operatively coupled to the micro-gearwheel pump 3 and, e.g., can be opened when a pumping operation is performed to enable fluid flow through the pipetting channel 2 or can be closed to inhibit fluid flow through the micro-gearwheel pump 3 as desired.

While not shown in FIG. 1, the pipetting system 1 further includes an automated positioning device to move the pipetting tip 4 of each of the pipetting channels 2. Since such positioning device is well-known to those of skill in the art it is not further elucidated herein.

In the pipetting system 1, the micro-gearwheel pump 3 can be operated at a wide range of nominal pumping flow rates extending over several order of magnitudes, e.g., ranging from several 10 µl/sec to several 10 ml/sec. Based on such a wide range of nominal flow rates, the pump 3 may advantageously be used for both pipetting fluids and washing the pipetting channels 2, for instance, by dispensing liquid system fluid 10 aspirated from the fluid reservoir 9 through the pipetting tip 4. Due to its construction, the micro-gearwheel pump 3 is subject to a leakage-caused fluid backflow as is now explained with particular reference to FIGS. 2A and 2B.

First, reference is made to FIG. 2A illustrating a cross-sectional view of the micro-gearwheel pump 3 of the pipetting system 1 of FIG. 1. Accordingly, the micro-gearwheel pump 3 includes two externally toothed gearwheels 18 which are accommodated in cavity 19 formed by pump housing 20. The gearwheels 18 are in meshing engagement to mutually turn in clockwise and counter-clockwise direction, respectively, wherein the rotational axes of the gearwheels 18 are offset and in parallel relationship with respect to each other. Together with an inner wall 22 of the cavity 19, an outer wall 23 of each of the gearwheels 18 circumferentially forms plural pressure chambers 21 cyclically changing their positions when the gearwheels 18 are rotated. The pressure chambers 21 are fluidically connected to the ports 6, 7 of the pump 3 to generate low-pulsation flows of fluid when turning the gearwheels 18.

As exemplified in FIG. 2A, the tip-sided port 6 may be used as outlet port for delivering liquid system fluid 10 towards the pipetting tip 4 while the reservoir-sided port 7 is used as inlet port for sucking system fluid 10 from the fluid reservoir 9 to generate a fluid flow having a nominal flow rate 25 towards the pipetting tip 4 to thereby generate a positive pressure in the pipetting tip 4 for dispensing fluid through the pipetting tip 4. The direction of flow can be reversed in changing the driving direction of the micro-gearwheel pump 3 by changing the turning direction of the meshing gearwheels 18 to generate a fluid flow towards the fluid reservoir 9 and to dispense system fluid 10 to the fluid reservoir 9 to thereby generate a negative pressure in the pipetting tip 4 for aspirating fluid into the pipetting tip 4.

Figure 2B:
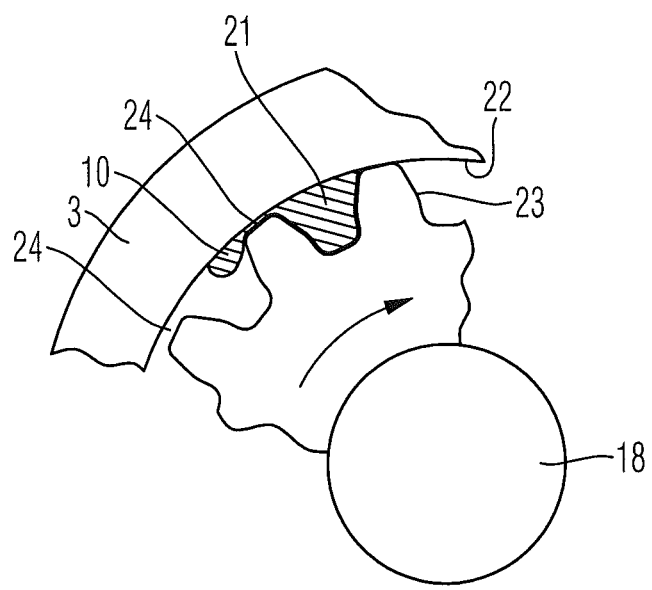

Reference is now made to FIG. 2B showing an enlarged detail of FIG. 2A illustrating the pressure chambers 21 of the (upper) gearwheel 18. As illustrated in FIG. 2B, since there is a fluidic connection to the ports 6, 7 and due to the necessity to turn the gearwheels 18 within the cavity 19, there are small gaps 24 present in-between the outer wall 23 of each of the gearwheels 18 and the inner wall 22 of the cavity 19 which become ever bigger the nearer the pressure chambers 21 are positioned to each of the ports 6, 7 when turning the gearwheels 18.

Figure 3:
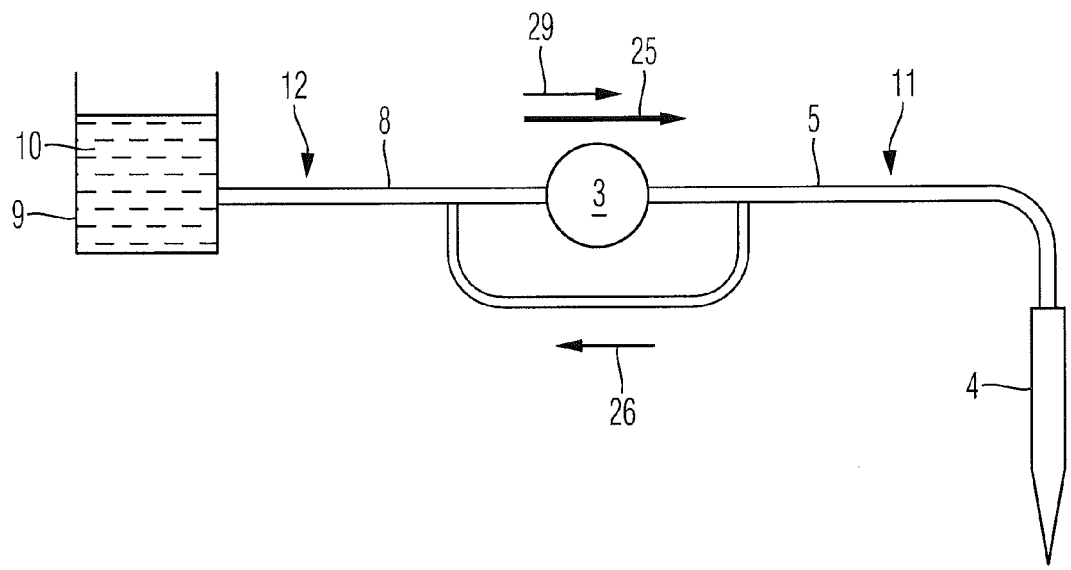
FIG. 3 depicts a schematic diagram illustrating leakage-caused fluid backflow of the micro-gearwheel pump of FIG. 1.

As schematically illustrated in FIG. 3 which is an equivalent diagram of the system of FIG. 1, as a result of these gaps 24 and dependent on atypically non-zero pressure difference between a fluid pressure in the tip-sided sub-channel 11 and a fluid pressure in the reservoir-sided sub-channel 12 arising during dispensation of fluid, a leakage-caused fluid backflow resulting in a fluid backflow having fluid backflow rate 26 flowing towards the system fluid reservoir 9 is superimposed to the pump-generated flow having nominal flow rate 25. Hence, the nominal flow rate 25 of the pump 3 is reduced by the fluid backflow rate 26 to result in a reduced (effective) flow rate 29.

Figure 4:
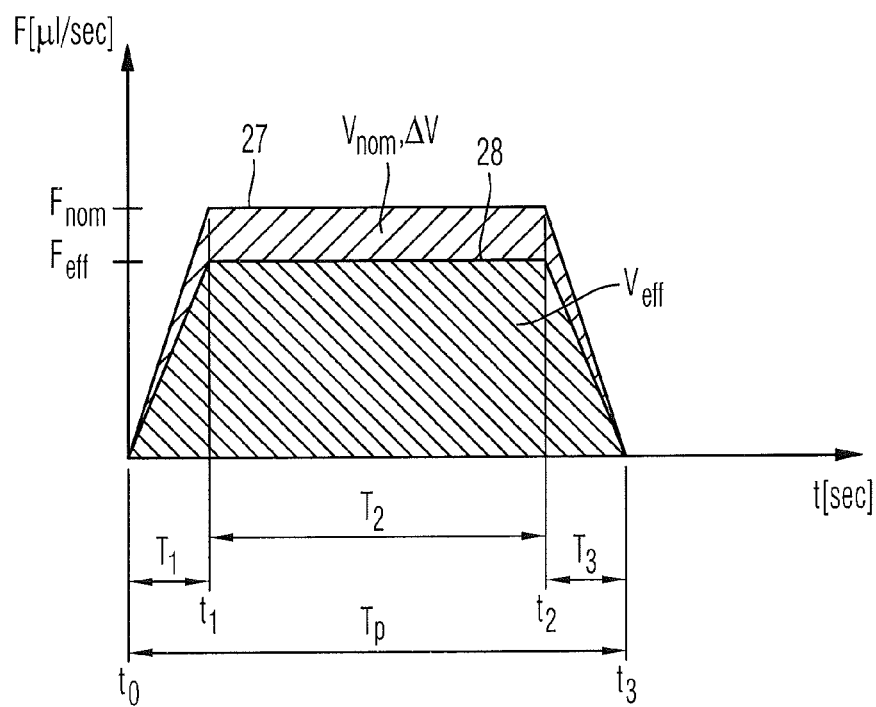
FIG. 4 depicts a schematic diagram illustrating a conventional pipetting operation.

Reference is now made to FIG. 4 illustrating a schematic diagram of a conventional pipetting operation in which a flow rate F in micro-liters per second [µl/sec] is drawn against time t in seconds [sec]. In FIG. 4, an upper curve 27 illustrates the hypothetic case of having a nominal flow rate $F_{nom}$ while a lower curve 28 illustrates the real case of having a reduced (effective) flow rate $F_{eff}$ reduced compared to the nominal flow rate $F_{nom}$ due to the fluid backflow of the micro-gearwheel pump 3.

As shown in FIG. 4, due to the finite starting and stopping operations of the micro-gearwheel pump 3, the pipetting operation may be divided into three time intervals, i.e. a first time interval $T_1$ in which the flow rate rises, a second time interval $T_2$ having constant flow rate and a third time interval $T_3$ in which the flow rate decreases. Specifically, with respect to the upper curve 27, in the first time interval $T_1$ ranging from $t=t_0$ to $t=t_1$ ($t_1>t_0$), the flow rate F increases from F=0 to $F=F_{nom}$, in the second time interval $T_2$ ranging from $t=t_1$ to $t=t_2$ ($t_2>t_1$), the flow rate F is constant ($F=F_{nom}$), and in the third time interval $T_3$ ranging from $t=t_2$ to $t=t_3$ ($t_3>t_2$), the flow rate F decreases from $F=F_{nom}$ to F=0. Analogously, with respect to the lower curve 28, in the first time interval $T_1$, the flow rate F rises from F=0 to $F=F_{eff}$ ($0<F_{eff}<F_{nom}$) in the second time interval $T_2$, the flow rate F is constant ($F=F_{eff}$) and in the third time interval $T_3$, the flow rate F decreases from $F=F_{eff}$ to F=0. Hence, the pipetting operation is performed in a total time interval $T_p$ ranging from $t=t_0$ to $t=t_3$ (in the introductory portion denoted as pipetting period). Specifically, an integrated area below the upper curve 27 indicates a nominal volume $V_{nom}$ which is to be pipetted and an integrated area below the lower curve 27 indicates a pipetted effective volume $V_{eff}$ reduced compared to the nominal volume $V_{nom}$ due to the leakage-caused fluid backflow. Hence, an area in-between the upper curve 27 and the lower curve 28 indicates a volume difference $\Delta V$, i.e. a lacking volume by which the nominal volume $V_{nom}$ has been reduced due to not achieving the nominal pumping flow rate $F_{nom}$ but only the effective pumping flow rate $F_{eff}$.

Figure 5:
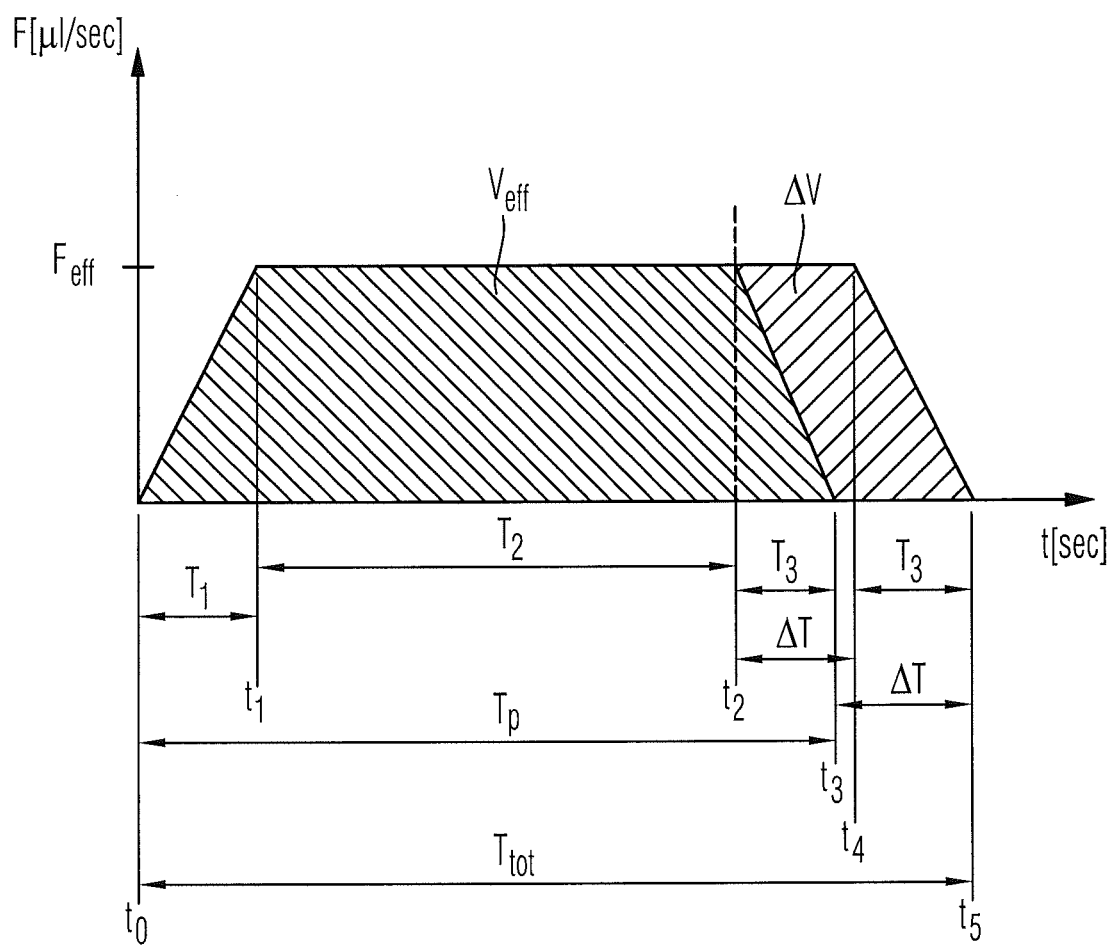
FIG. 5 depicts a schematic diagram illustrating an exemplary embodiment of a pipetting operation according to the invention.
Figure 6:
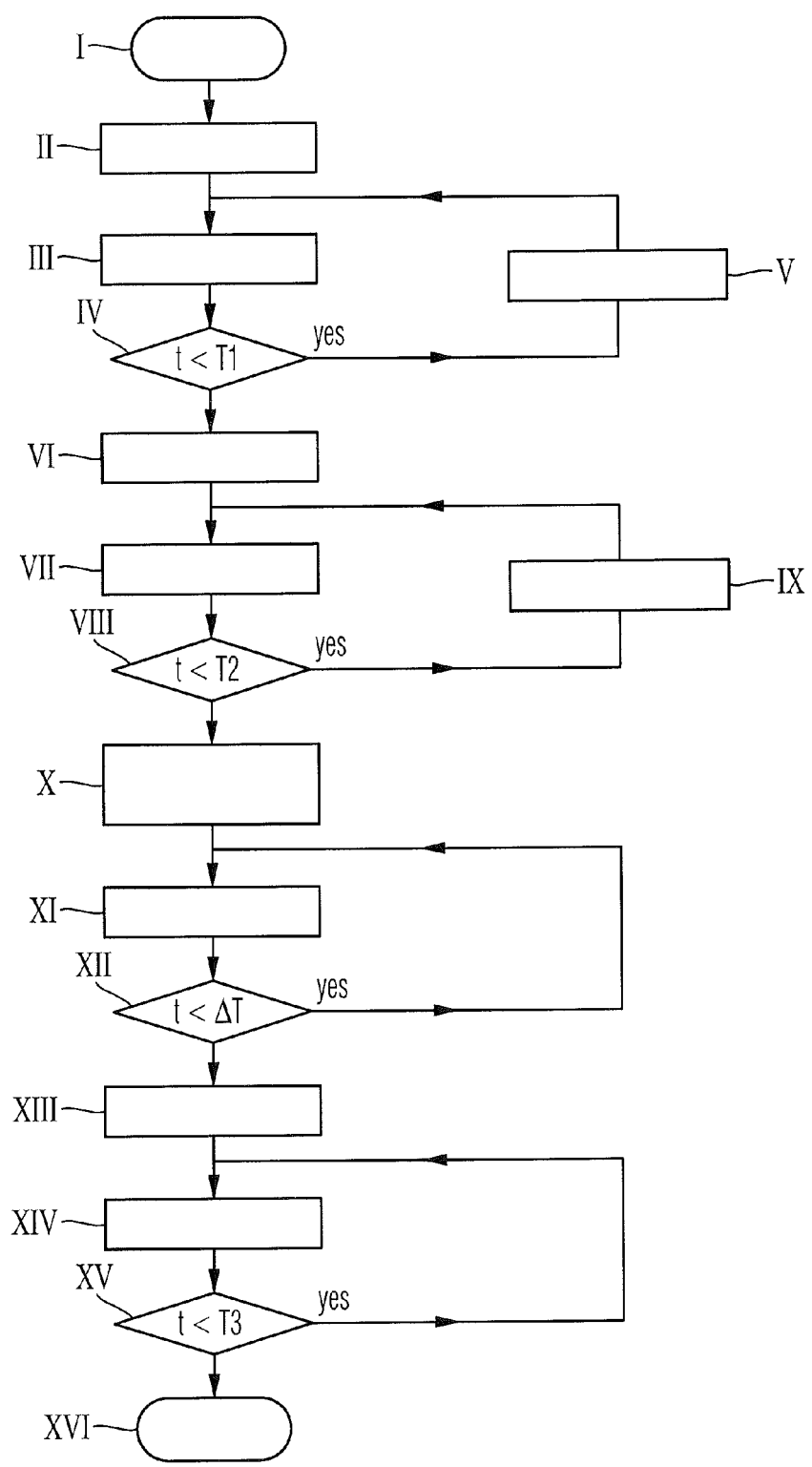
FIG. 6 depicts a flowchart describing an exemplary embodiment of a method for pipetting fluid according to the invention using the system of FIG. 1.

Now referring to FIG. 5 and FIG. 6 an exemplary embodiment of the method for pipetting of fluids according to the invention is explained.

Reference is first made to FIG. 5 illustrating an exemplary pipetting operation for the pipetting of a nominal fluid volume $T_{nom}$. Accordingly, the pipetting operation is performed during an extended time interval $T_{tot}$ (in the introductory portion denoted as extended pipetting period) ranging from $t=t_0$ to $t=t_5$ by operating the micro-gearwheel pump 3 at the nominal flow rate $F_{nom}$ resulting in the reduced effective flow rate $F_{eff}$ due to the fluid backflow. Specifically, the pipetting operation includes the first time interval $T_1$ ranging from $t=t_0$ to $t=t_1$ ($t_1>t_0$) having a rising flow rate (increasing ramp) increasing from F=0 to the effective flow rate $F_{eff}$, the second time interval $T_2$ ranging from $t=t_1$ to $t=t_2$ ($t_2>t_1$) having constant effective flow rate $F_{eff}$, a third time interval $\Delta T$ ranging from $t=t_2$ to $t=t_4$ ($t_4>t_2$) also having constant effective flow rate $F_{eff}$ and a fourth time interval $T_3$ ranging from $t=t_4$ to $t=t_5$ ($t_5>t_4$) having a falling flow rate (decreasing ramp) decreasing from the effective flow rate $F_{eff}$ to F=0. Accordingly, the extended time interval $T_{tot}$ is composed of the pipetting period $T_p$ derived from the nominal flow rate $F_{nom}$ in order to pipette the nominal volume $V_{nom}$ and a further time interval $\Delta T$ (in the introductory portion called period extension) ranging from $t=t_3$ to $t=t_5$ (equivalently ranging from $t=t_2$ to $t=t_4$). Hence, the pipetting period $T_p$ (calculated based on the nominal flow rate $F_{nom}$) is extended by the period extension $\Delta T$ considering that the nominal flow rate $F_{nom}$ is reduced by the leakage-caused fluid backflow of the micro-gearwheel pump 3. Since the second time interval $T_2$ is immediately extended by the period extension $\Delta T$ having the same effective flow rate $F_{eff}$, the extended pipetting period $T_{tot}$ has a single rising ramp and a single falling ramp.

In order to pipette the nominal volume $V_{nom}$ as desired, the period extension $\Delta T$ is adapted for pipetting of the volume difference $\Delta V$. Accordingly, the nominal volume $V_{nom}$ is pipetted during the extended pipetting period $T_{tot}$ considering that the micro-gearwheel pump 3 can only achieve the effective pumping flow rate $F_{eff}$ when operated at the nominal flow rate $F_{nom}$.

In the following, assuming that a nominal fluid volume $V_{nom}$ is to be pipetted, an exemplary calculation of the extended pipetting period $T_{tot}$ is described.

Provided that the pump is operated at the nominal flow rate $F_{nom}$, a pipetting period $T_p$ (without fluid backflow) is given by:

$$T_p = V_{nom}/F_{nom} \quad (1).$$

During the pipetting period $T_p$, due to the leakage-caused fluid backflow rate $F_{back}$ resulting in effective flow rate $F_{eff}$, the following volume difference $\Delta V$ is not pipetted:

$$\Delta V = T_p \cdot F_{back} \quad (2).$$

In order to pipette the lacking volume difference $\Delta V$, the following time span $\Delta T$ (period extension) is required:

$$\Delta T = \Delta V/F_{eff} = T_p \cdot F_{back}/F_{eff} \quad (3).$$

Using definition of the effective flow rate $F_{eff}$ being equal to the nominal flow rate $F_{nom}$ reduced by the backflow rate $F_{back}$, i.e.

$$F_{eff} = F_{nom} - F_{back} \quad (4)$$

yields:

$$\Delta T = T_p \cdot F_{back}/(F_{nom} - F_{back}) \quad (5).$$

Now assuming that there is a linear relationship between the backflow rate $F_{back}$ and the pressure difference $\Delta p$ between fluid pressures downstream and upstream the pump, i.e.

$$F_{back} = k \cdot \Delta p \quad (6),$$

where equation (5) can be written as:

$$\Delta T = T_p \cdot k \cdot \Delta p/(F_{nom} - k \cdot \Delta p) \quad (7).$$

Using equation (1), equation (7) can be written as:

$$\Delta T = V_T \cdot k \cdot \Delta p/(F_{nom} \cdot (F_{nom} - k \cdot \Delta p)) \quad (8).$$

In equation (8), constant k is determined using a calibration routine as detailed below, the nominal flow rate $F_{nom}$ is known from the manufacturer or may be readily determined using a rotary encoder, and, the pressure difference $\Delta p$ is determined as detailed below.

Accordingly, the period extension $\Delta T$ as well as the extended pipetting period $T_{tot} = T_p + \Delta T$ can be determined using equation (8).

Now with particular reference to FIG. 6 illustrating a flowchart, an exemplary method for performing a pipetting operation as illustrated in FIG. 5 is explained.

Following initiation of the process (step I), the pipetting operation for the automated dispensation of fluid begins with starting and accelerating rotational movement of the gearwheels 18 of the micro-gearwheel pump 3 (step II).

After continuing acceleration for a predetermined time span (step III), it is checked (step IV) whether the elapsed time is smaller than the first time interval $T_1$ ($t < T_1$). If yes, then the pressure difference $\Delta p$ between fluid pressures in the tip tubing 5 and the reservoir tubing 8 is determined and stored in a memory (step V) and acceleration of the rotational movement of the gearwheels 18 continues for another time span P. If no, then acceleration of the gearwheels 18 stops and the gearwheels 18 are turned with constant turning speed to result in a nominal flow rate $F_{nom}$ which actually is reduced to the effective flow rate $F_{eff}$ due to the fluid backflow (step VI).

After continuing turning the gearwheels 18 with constant turning speed for another predetermined time span P (step VII), it is checked (step VIII) whether the elapsed time is smaller than the second time interval $T_2$ ($t < T_2$). If yes, then the pressure difference $\Delta p$ between a fluid pressure in the tip tubing 5 and the reservoir tubing 8 is determined and stored in the memory (step IX) and turning of the gearwheels 18 of the pump 3 with constant turning speed continues for another time span P. If no, then the period extension $\Delta T$ is calculated (step X) as above-detailed and rotation of the gearwheels 18 is continued with the same constant turning speed during the period extension $\Delta T$ without time gap in-between the second time interval $T_2$ and the period extension $\Delta T$, i.e., without deceleration of the gearwheels 18.

After continuing turning the gearwheels 18 with the constant turning speed for another predetermined time span P (step XI), it is checked (step XII) whether the elapsed time is smaller than the period extension $\Delta T$ ($t < \Delta T$). If yes, then the gearwheels 18 of the pump 3 are further rotated with constant turning speed for another time span P. If no, then deceleration of the gearwheels 18 of the pump 3 starts (step XIII).

After continuing deceleration for another predetermined time span (step XIV), it is checked (step XV) whether the elapsed time is smaller than the third time interval $T_3$ ($t < T_3$). If yes, then deceleration of the gearwheels 18 of the pump 3 continues for another time span P. If no, then the process ends (step XVI).

Accordingly, in above process, the nominal volume $V_{nom}$ is dispensed through the pipetting tip 4 by operating the micro-gearwheel pump 3 during an extended pipetting period $T_{tot}$ composed of the pipetting period $T_p$ and the period extension $\Delta T$, i.e. $T_{tot} = T_p + \Delta T$, at the nominal flow rate $F_{nom}$ reduced to the effective flow rate $F_{eff}$ due to the leakage-caused fluid backflow. The second time interval $T_2$ starts after elapse of the first time interval $T_1$ without time gap in-between the first time interval $T_1$ and the second time interval $T_2$. The period extension $\Delta T$ starts after elapse of the second time interval $T_2$ without time gap in-between the second time interval $T_2$ and the period extension $\Delta T$. The third time interval $T_3$ starts after elapse of the period extension $\Delta T$ without time gap in-between the period extension $\Delta T$ and the third time interval $T_3$.

Figure 7A:
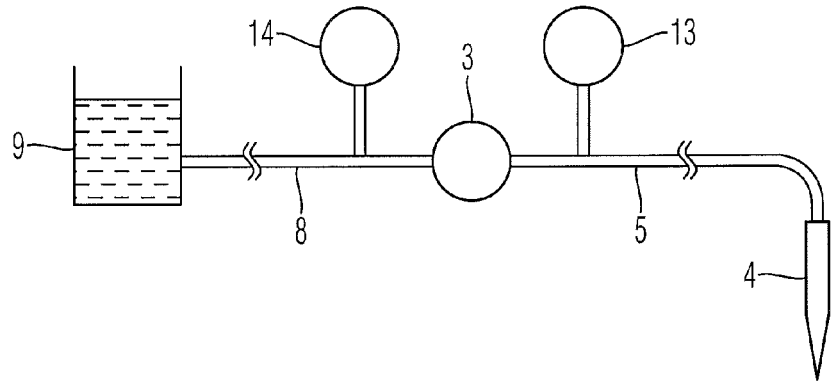
FIGS. 7A-7D depict schematic diagrams illustrating determination of pressure differences in the system of FIG. 1.

In above process described in connection with FIG. 6, in step X, the period extension $\Delta T$ is determined based on measuring a tip-sided fluid pressure in the tip tubing 5 by means of tip-sided pressure sensor 13 and measuring a reservoir-sided fluid pressure in the reservoir tubing 8 by means of reservoir-sided pressure sensor 14, followed by calculating a pressure difference $\Delta p$ between the tip-sided fluid pressure and the reservoir-sided fluid pressure in step V and in step IX. In FIG. 7A which is a schematic equivalent diagram of the system 1 of FIG. 1, determination of the pressure difference $\Delta p$ by means of pressure sensors 13, 14 is illustrated.

Figure 7B:
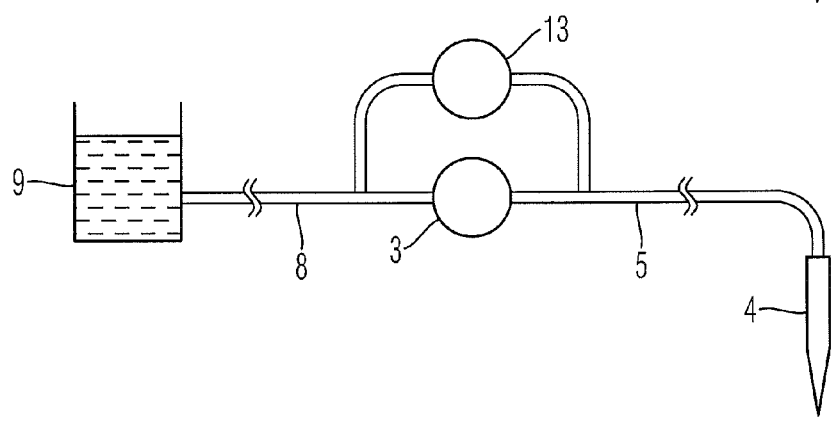

As illustrated in FIG. 7B which is another schematic equivalent diagram of the system 1 of FIG. 1, according to an alternative method embodiment of the invention, the pressure difference $\Delta p$ between the tip-sided fluid pressure and the reservoir-sided fluid pressure may be determined in measuring the tip-sided fluid pressure by means of tip-sided pressure sensor 13 and further assuming that the fluid pressure in the reservoir tubing 8 has a constant value, e.g., zero.

Figure 7C:
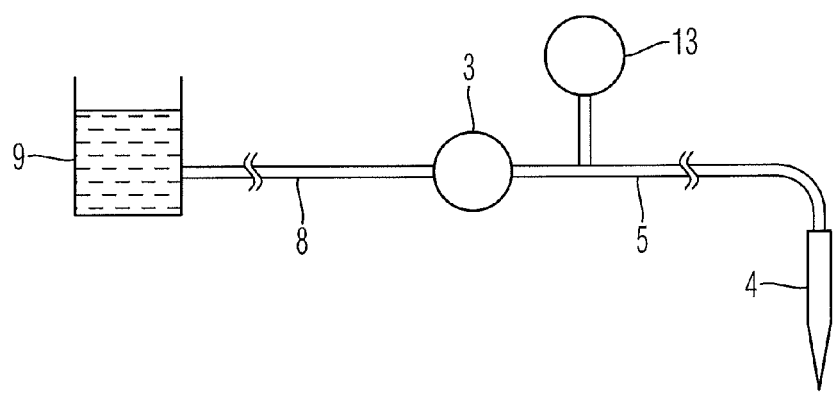

As illustrated in FIG. 7C which is a yet another schematic equivalent diagram of the system 1 of FIG. 1, in a yet alternative method embodiment of the invention, the pressure difference $\Delta p$ between the tip-sided fluid pressure and the reservoir-sided fluid pressure may be determined in measuring the tip-sided fluid pressure by means of tip-sided pressure sensor 13 and determining the fluid pressure in the reservoir tubing 8 by means of a calculation model which is based on parameters of the reservoir tubing 8 and pump 3 and parameters of the fluid such as fluid temperature. The fluid temperature may, e.g., be measured by a temperature sensor.

Figure 7D:
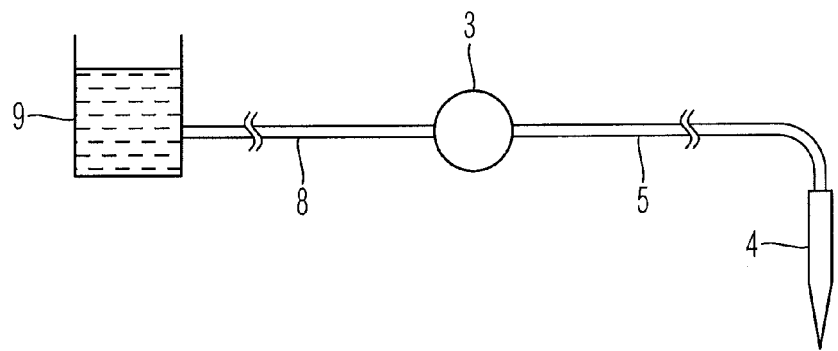

As illustrated in FIG. 7D, which is a yet another schematic equivalent diagram of the system 1 of FIG. 1, in a yet alternative method embodiment of the invention, the pressure difference $\Delta p$ between the tip-sided fluid pressure and the reservoir-sided fluid pressure may be determined in determining both the tip-sided fluid pressure and the reservoir-sided fluid pressure by a calculation model based on parameters of the tip tubing 5, the reservoir tubing 8 and pump 3 and parameters of the fluid such as fluid temperature. The fluid temperature may, e.g., be measured by a temperature sensor.

Figure 8:
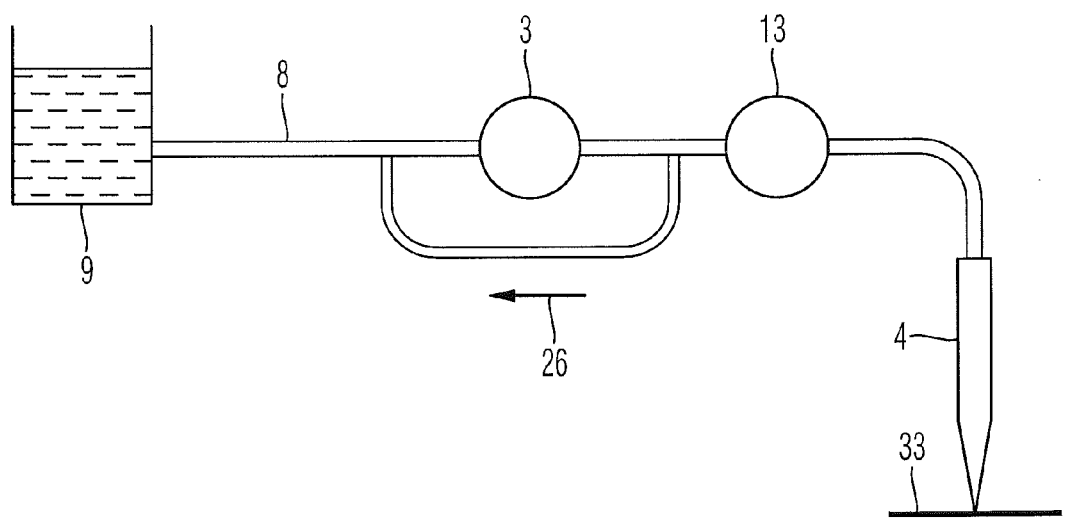
FIG. 8 depicts a schematic diagram illustrating calibration of the system of FIG. 1.

With reference to FIG. 8 illustrating a schematic equivalent diagram of the system 1 of FIG. 1, an exemplary embodiment of the method for calibration the pipetting system 1 is explained. The calibration routine can be performed prior to starting the pipetting operations and may, e.g., be performed in a periodic manner and/or each time the pipetting system 1 is initialized.

As illustrated in FIG. 8, in order to calibrate the system 1, fluid flow through the micro-gearwheel pump 3 is inhibited by placing the pipetting tip 4 onto a tip blocker 33 which externally blocks the pipetting tip 4 so that the pipetting fluid may not be dispensed or aspirated through the pipetting tip 4. Alternatively, the fluid valve 15 could be closed to inhibit fluid flow through the micro-gearwheel pump 3.

Figure 9:
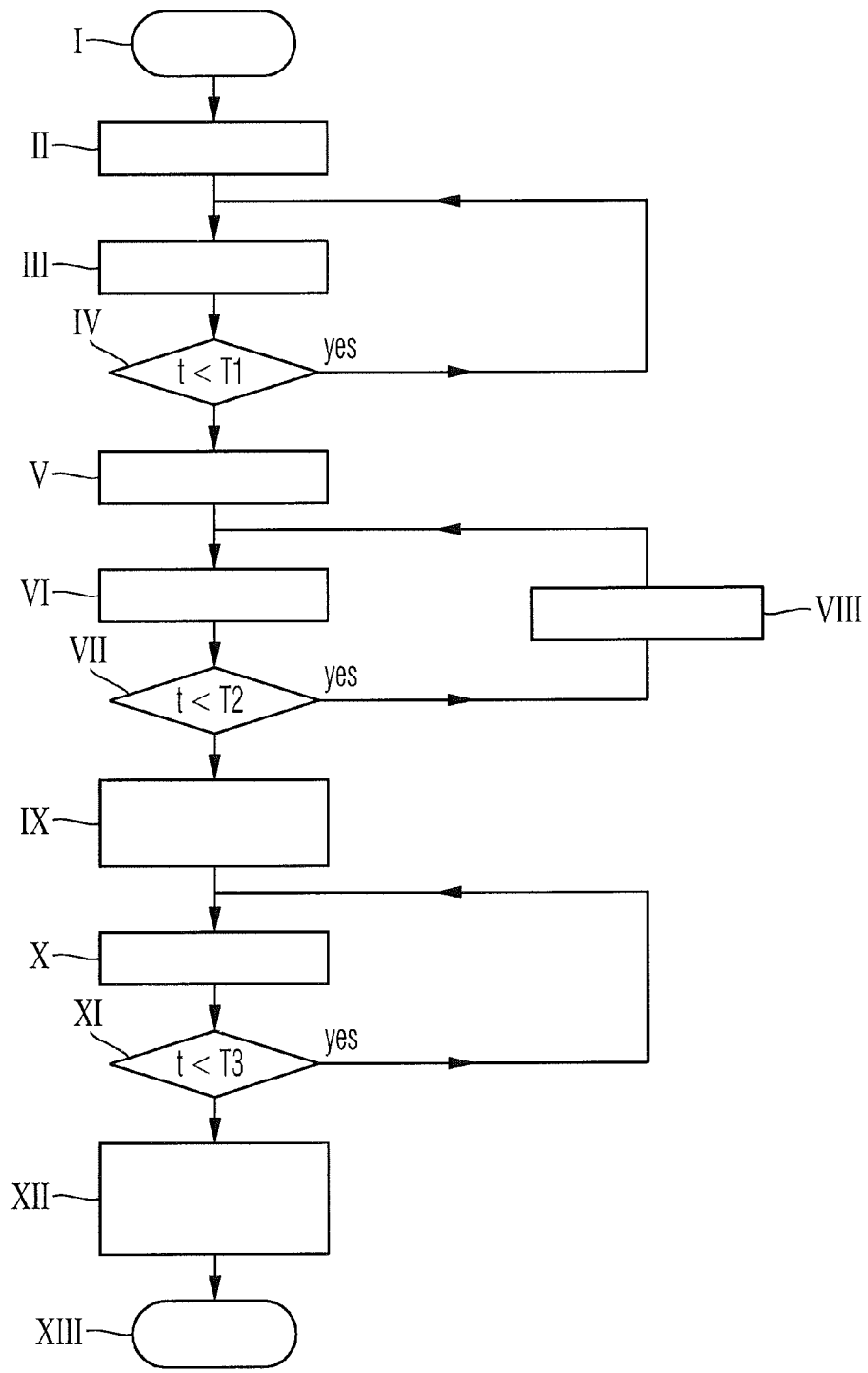
FIG. 9 depicts a flowchart describing an exemplary embodiment of a method for calibrating the system of FIG. 1 according to the invention.

With particular reference to FIG. 9, following initiation of the process (step I), the calibration routine begins with starting and accelerating rotational movement of the gearwheels 18 of the micro-gearwheel pump 3 to generate a fluid flow towards the pipetting tip 4 (step II).

After continuing acceleration for a predetermined time span (step III), it is checked (step IV) whether the elapsed time is smaller than the first time interval $T_1$ ($t<T_1$). If yes, then acceleration of the rotational movement of the gearwheels 18 continues for another time span P. If no, then acceleration of the gearwheels 18 of the pump 3 stops and the gearwheels 18 are turned with constant turning speed resulting in a blocked-condition nominal flow rate $F'_{nom}$ (step V) which is identified as fluid backflow rate. In other words, the pump is brought in an operating condition which without blocked pipetting tip would result in the nominal flow rate $F_{nom}$ which, however, due to the blocked pipetting tip results in a blocked-condition nominal flow rate $F'_{nom}$ (in the following "'" denotes the blocked condition of the pipetting tip).

After continuing turning the gearwheels 18 with constant turning speed for another predetermined time span P (step VI), it is checked (step VII) whether the elapsed time is smaller than the second time interval $T_2$ ($t<T_2$). If yes, then the pressure difference $\Delta p$ between a fluid pressure in the tip tubing 5 and the reservoir tubing 8 is determined and stored in the memory (step VIII) and turning the gearwheels 18 of the pump 3 with constant turning speed continues for another time span P. If no, then deceleration of the gearwheels 18 of the pump 3 starts (step IX).

After continuing deceleration for another predetermined time span (step X), it is checked (step XI) whether the elapsed time is smaller than the third time interval $T_3$ ($t<T_3$). If yes, then deceleration of the gearwheels 18 of the pump 3 continues for another time span P. If no, then a linear relationship between fluid backflow and pressure difference in the tip and reservoir tubings 5, 8 is established (step XII). After that, the process ends (step XIII).

In above calibration routine, in order to determine a linear relationship between fluid backflow and pressure difference in step XII, a pressure difference between fluid pressures in the tip and reservoir tubings 5, 8 is determined by measuring the fluid pressure in the tip tubing 5 by means of the tip-sided pressure sensor 13 and by measuring the fluid pressure in the reservoir tubing 8 by means of the reservoir-sided pressure sensor 14 in step VIII. Alternatively, the fluid pressure in the reservoir tubing 8 can be determined by means of a calculation model, or yet alternatively, in setting the fluid pressure to have a predetermined constant value such as zero.

Based on the tip- and reservoir-sided fluid pressures, a fluid pressure difference $\Delta p'$ is calculated which is considered as "maximum fluid pressure difference". Furthermore, the nominal flow rate $F'_{nom}$ of the micro-gearwheel pump 3 pumping against the blocked pipetting tip 4 is determined which, e.g., can be readily performed in determining a rotational speed of the gearwheels 18 by means of a rotary encoder (not illustrated). Determining the blocked-condition nominal flow rate $F'_{nom}$ of the micro-gearwheel pump 3 pumping against the blocked pipetting tip 4 may, e.g., be performed in step VIII. The blocked-condition nominal flow rate $F'_{nom}$ obtained is identified as maximum backflow rate occurring in case of maximum fluid pressure difference. Furthermore, a minimum fluid backflow rate, e.g. zero, occurring in case of minimum pressure difference, e.g. zero, is defined.

Figure 10A:
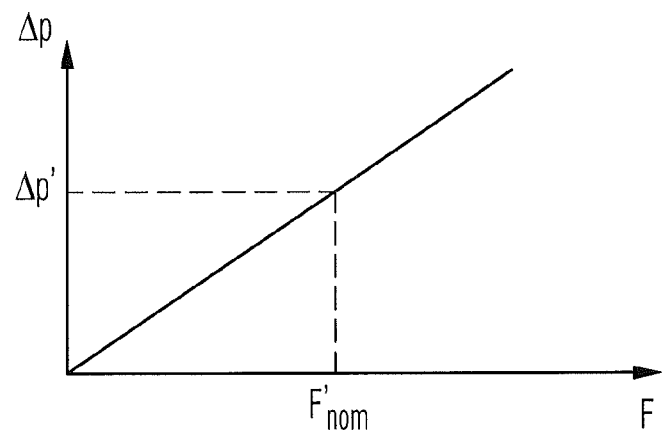
FIGS. 10A-10B depict schematic diagrams illustrating linear relationships between pressure differences and fluid backflows.

After that, a linear relationship between the maximum fluid backflow assigned to the maximum pressure difference and the minimum fluid backflow assigned to the minimum pressure difference can be obtained as illustrated in FIG. 10A.

Figure 10B:
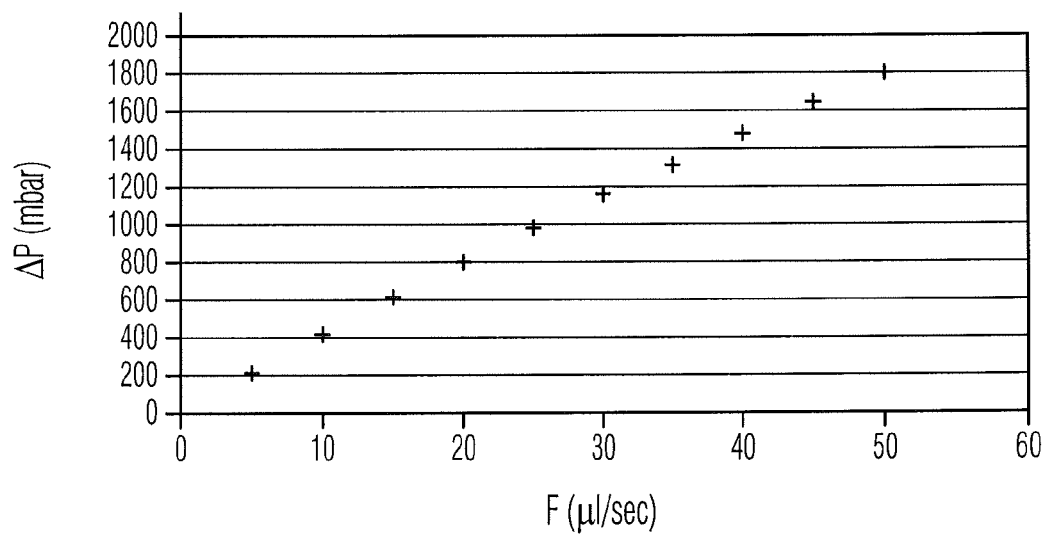

Alternatively, in above method, steps I to XIII can be performed in operating the pump at plural nominal flow rates $F_{nom}$ which due to the blocked pipetting tip results in plural blocked-condition nominal pumping flow rates $F'_{nom}$ which are identified as fluid backflow rates. Analogously, in FIG. 10B, an exemplary linear relationship between the pressure differences $\Delta P$ (mbar) and fluid backflow rates F (μl/sec) is illustrated.

Basically, constant k of above equation (8) used for determining the period extension $\Delta T$ may be derived as follows:

Assuming that the fluid backflow rate $F'_{back}$ is equal to the nominal flow rate $F'_{nom}$ ($F_{eff}=0$) in the tip-blocked condition, the fluid back flow rate is given by:

$$F'_{back}=k \cdot \Delta p'=F'_{nom} \quad (9).$$

Hence, constant k can be written as:

$$k=\Delta p'/F'_{nom} \quad (10).$$

In equation (10), the pressure difference $\Delta p'$ can be determined as above-detailed. The blocked-condition nominal flow rate $F'_{nom}$ can be determined in determining the rotational speed of the gearwheels 18 by means of the rotary encoder. Accordingly, equation (10) can be used to determine constant k.

Figure 11:
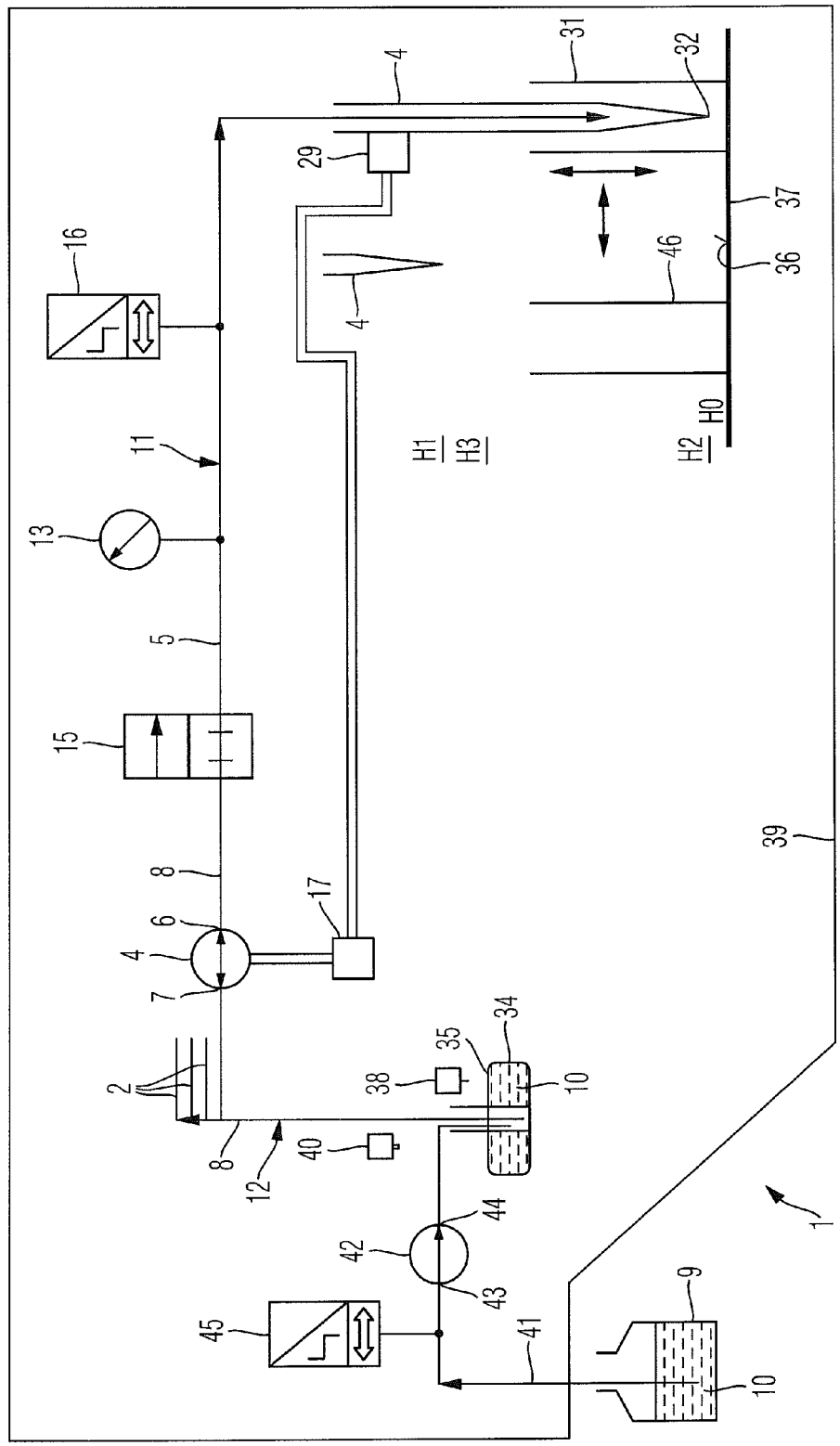
FIG. 11 depicts a schematic diagram of another exemplary embodiment of a pipetting system according to the invention.
Figure 12:
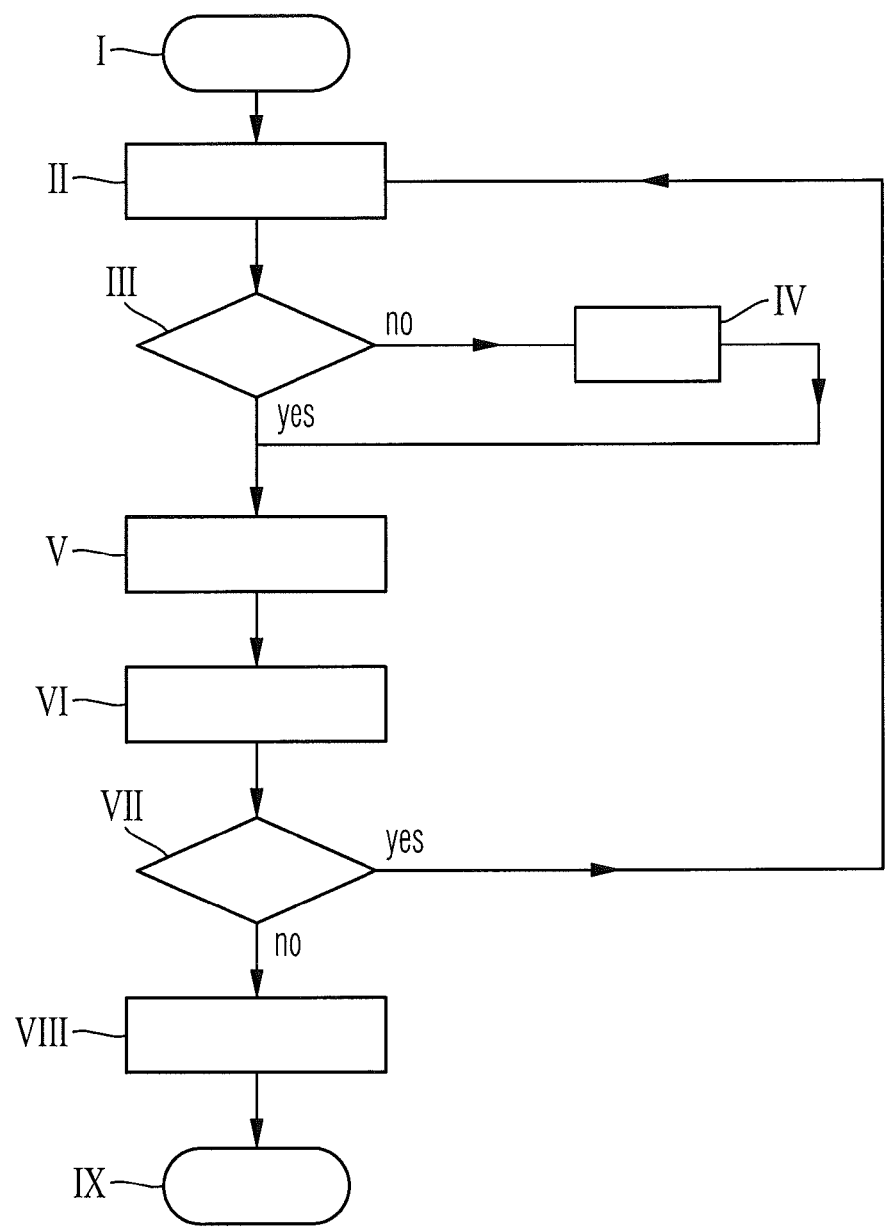
FIG. 12 depicts a flowchart describing an exemplary embodiment of a method for pipetting of fluid according to the invention using the system of FIG. 11.

Now referring to FIG. 11 and FIG. 12, another exemplary embodiment of the system 1 and method for the automated pipetting of fluids is explained. In order to avoid unnecessary repetitions, only differences with respect to the system of FIG. 1 are explained and otherwise reference is made to the description made in connection with FIG. 1.

With particular reference to FIG. 11, the system 1 includes an intermediate reservoir 34 for liquid system fluid 10 which is fluidically interconnected between the system fluid reservoir 9 and the micro-gearwheel pump 3. As illustrated, the intermediate reservoir 34 is at least partly filled with liquid system fluid 10. The fluid level (in FIG. 1 denoted as "H3") of the intermediate reservoir 34 given by a vertical position of an upper fluid surface 35 relates to a reference level (in FIG. 1 denoted as "H0") which, e.g., may be defined by an upper surface 36 of a work-plate 37. The fluid level of the liquid system fluid 10 is measured by a fluid level sensor 38 which, e.g., may be embodied as ultrasonic sensor adapted for determining the fluid level by means of acoustic waves. Ultrasonic sensors for emitting acoustic waves towards a fluid level and receiving acoustic waves returning upon reflection at the fluid surface are well-known to those of skill in the art and thus need not be further elucidated herein.

In the system 1, the intermediate reservoir 34 is accommodated in a partially or fully closed housing 39 shielding the components contained therein from external influences. Accordingly, the intermediate reservoir 34 maybe considered an internal reservoir of the liquid system fluid 10.

The pipetting system 1 further includes an ultraviolet light (UV) emitting lamp 40 adapted to inhibit growth of microbes in the intermediate reservoir 34. Additionally or alternatively, a microbe filter adapted to filter microbes may be placed in the reservoir-sided pump tubing 8. Yet alternatively, liquid system fluid 10 contained in the intermediate reservoir 34 may be preserved by an antimicrobial agent.

The intermediate reservoir 34 is fluidically connected to the system fluid reservoir 9 by means of a, e.g. plastic-made, flexible reservoir tubing 41. A reservoir pump 42 is fluidically inter-connected between the intermediate reservoir 34 and the system fluid reservoir 9. Stated more particularly, the reservoir tubing 41 is connected to an inlet port 43 and an outlet port 44 of the reservoir pump 42. The reservoir pump 42 can be uni-directionally operated for transferring system liquid fluid 10 from the system fluid reservoir 9 to the intermediate reservoir 34.

The pipetting system 1 further includes another sensor arrangement, in the following denoted as "reservoir sensor arrangement 45" positioned at the reservoir tubing 41 and comprising plural sensors adapted for sensing physical parameters of the liquid system fluid 10, including an optical flow sensor adapted for sensing a fluid flow in the reservoir tubing 41. While the reservoir pump 42 and the reservoir sensor arrangement 45 are accommodated in the housing 39, the system fluid reservoir 9 is positioned outside the housing 39. Accordingly, the system fluid reservoir 9 is an external reservoir with respect to the housing 39.

The pipetting system 1 further includes an automated positioning device 30 adapted to move the pipetting tip 4 of each of the pipetting channels 2 with respect to tubes 46 placed on the horizontal work-plate 37. The pipetting tips 4 of the pipetting channels 2 may, e.g., be mounted to a transfer head which can be moved towards and away from the work-plate 37, e.g., by means of a spindle drive, and in a horizontal plane over the work-plate 37, e.g., by means of guiding rails as indicated by the arrows. Since such positioning device is well-known to those of skill in the art, it is not further detailed herein.

The pipetting tip 4 may, e.g., be moved in a first vertical position in which an orifice 32 of the pipetting tip 4 has a first height (in FIG. 11 denoted as "H1") above the fluid level H3 of the intermediate reservoir 34 and in a second vertical position in which the orifice 32 has a second height (in FIG. 1 denoted as "H2") lower than the first vertical position (H2<H1) and below the fluid level H3 of the intermediate reservoir 34. The first vertical position may, e.g., be used for moving the pipetting tip from one tube 31 to another tube 31 and the second vertical position may, e.g., be used for dispensing fluid to the tubes 31.

With particular reference to FIG. 12 illustrating a flow-chart, an exemplary embodiment for pipetting of fluids using the system of FIG. 11 is explained.

Following initiating of the process (step I), a fluid level of liquid system fluid 10 contained in the intermediate reservoir 34 is measured using the fluid level sensor 38 (step II).

Based on the fluid level obtained, it is checked (step III) whether the fluid level of the liquid system fluid 10 matches a predetermined target fluid level. In the following it is assumed that the target fluid level is reached at the height H3 as indicated in FIG. 11. If no, then liquid system fluid 10 is transferred from the system fluid reservoir 9 to the intermediate reservoir 34 by operating the reservoir pump 42 until the target fluid level is reached (step IV).

If yes, a pipetting operation for the pipetting of fluid is initiated by moving the pipetting tip 4, e.g. from a parking position, to an intended pipetting position with respect to the tubes 31 (step V). In step V, before starting horizontally moving the pipetting tip 4 over the work-plate 37, the pipetting tip 4 is brought in a vertical position so that the orifice 32 of the pipetting tip 4 is in the first vertical position having height H1 to thereby generate a negative hydrostatic pressure in the pipetting tip 4.

Having the intended pipetting position reached, the pipetting tip 4 is lowered so that the orifice 32 of the pipetting tip 4 is in the second vertical position having height H2 and the pipetting operation, e.g. dispensing of fluid, is performed (step VI). Then pipetting of fluid is performed as explained in connection with FIGS. 5 and 6.

Next it is checked, whether another pipetting operation has to be performed (step VII). If yes, then the process goes back to step II to measure the fluid level of liquid system fluid 10 contained in the intermediate reservoir 34. The intermediate reservoir 34 is re-filled in case of lower fluid level with respect to the target fluid level, followed by moving the pipetting tip 4 in the intended pipetting position (step V). In that, prior to starting a horizontal movement of the pipetting tip 4 over the work-plate 37, the pipetting tip 4 is brought in the first vertical position so that the orifice 32 of the pipetting tip 4 has height H1 to generate a negative hydrostatic pressure in the pipetting tip 4 to avoid dropping of fluid contained in the pipetting tip 4, followed by lowering the pipetting tip 4 in the intended pipetting position so that the orifice 32 of the pipetting tip 4 is in the second vertical position having height H2. After that, the pipetting operation is performed (step VI).

If no, then the pipetting tip 4 is, e.g., brought in a parking position (step VIII). In step VIII, prior to starting a horizontal movement of the pipetting tip 4 over the work-plate 37, the pipetting tip 4 is brought in the first vertical position so that the orifice 47 of the pipetting tip 4 has height H1 to thereby generate a negative hydrostatic pressure in the pipetting tip 4 in order to avoid dropping of pipetting fluid contained in the pipetting tip 4.

After that, the process terminates (step IX).

Accordingly, in the method embodiment exemplified in connection with FIG. 12, the fluid level of the liquid system fluid 10 contained in the intermediate reservoir 34 is kept on the target fluid level H3 to realize an invariant fluid level during the whole pipetting operation. The orifice 32 of the pipetting tip 4 is brought in a higher position with respect to the target fluid level when moving the pipetting tip 4 over the work-plate 37 to generate a negative hydrostatic pressure in the pipetting tip 4 in order to avoid dropping of fluid contained in the pipetting tip 4 and, in pipetting position, is lowered below the target fluid level for aspirating or dispensing fluid.

The fluid level of the liquid system fluid 10 contained in the intermediate reservoir 34 is kept invariant with respect to a vertical position of the micro-gearwheel pump 3, as, e.g., defined by a vertical position of the reservoir-sided port 7 with respect to the reference level HO. Due to an invariant hydrostatic pressure of the liquid system fluid 10 in the intermediate reservoir 34, precision of pipetting operations can advantageously be increased.

Alternatively, instead of using the fluid level sensor 38, the fluid level may be indirectly determined by means of fluid flow sensors included in the sensor arrangements 16, 45 measuring fluid flow streaming in and out of the intermediate reservoir 34.

In the system 1 for the automated processing of fluids, the system fluid reservoir 9 may be readily replaced during an ongoing run for pipetting of fluids, e.g., in case of an empty fluid reservoir 9. While not shown in FIG. 11, instead of a single external system fluid reservoir 9, a plurality of system fluid reservoirs 9 may be provided which may contain different liquid system fluids.

Obviously many modifications and variations of the present invention are possible in light of the above description. It is therefore to be understood, that within the scope of appended claims, the various embodiments of the invention may be practiced otherwise than as specifically devised.

What is claimed is:

1. A pipetting system comprising:
   at least one pipetting channel for pipetting of fluids including a channel pump having at least one tip-sided port connected to a pipetting tip by a tip-sided pump conduit which generates a positive or negative pressure in said pipetting tip and at least one reservoir-sided port connected to a system fluid reservoir by a reservoir-sided pump conduit, said channel pump exhibiting a fluid backflow caused by a pressure difference in the tip- and reservoir-sided pump conduits resulting in an effective flow rate ($F_{\mathit{eff}}$) compared to a nominal flow rate ($F_{nom}$); and
   a controller which:
   determines a pressure difference ($\Delta p$) between said tip- and reservoir-sided pump conduits;
   based on said pressure difference ($\Delta p$), determines a volume difference ($\Delta V$) between a nominal volume ($V_{nom}$) and an effective volume ($V_{\mathit{eff}}$) pipetted by operating the channel pump during a pipetting period ($T_p$) at said nominal flow rate ($F_{nom}$), said effective volume ($V_{\mathit{eff}}$) being reduced compared to said nominal volume ($V_{nom}$) due to said fluid backflow;
   based on said determined volume difference ($\Delta V$), determines a period extension ($\Delta T$), the period extension ($\Delta T$) being adapted for pipetting of said volume difference ($\Delta V$); and
   pipettes fluid by operating said channel pump at said nominal flow rate ($F_{nom}$) during an extended pipetting period ($T_{tot}$) which extends said pipetting period ($T_p$) by said period extension ($\Delta T$).

2. The pipetting system according to claim 1, further comprising a fluid pressure sensor which senses fluid pressure downstream of said channel pump.

3. The pipetting system according to claim 1, further comprising a fluid flow inhibiting device arranged downstream of said channel pump to inhibit fluid flow through said channel pump.

4. The pipetting system according to claim 1, further comprising a temperature sensor which senses fluid temperature in said pipetting channel.

5. The pipetting system according to claim 1, further comprising at least one intermediate reservoir fluidically interconnected between said system fluid reservoir and said channel pump which transfers fluid from said system fluid reservoir to said intermediate reservoir so as to have an invariant fluid level in said intermediate reservoir.

6. The pipetting system according to claim 5, further comprising a reservoir pump fluidically interconnected between said system fluid reservoir and said intermediate reservoir wherein said controller controls transfer of fluid from said system fluid reservoir to said intermediate reservoir so as to have an invariant fluid level in said intermediate reservoir.

7. The pipetting system according to claim 5, further comprising a positioning device for positioning said pipetting tip wherein said controller controls movement of said pipetting tip with respect to said invariant fluid level of said intermediate reservoir.

8. A method for pipetting of fluids comprising:
   providing a pipetting system comprising at least one pipetting channel for pipetting of fluids including a channel pump having at least one tip-sided port connected to a pipetting tip by a tip-sided pump conduit which generates a positive or negative pressure in said pipetting tip and at least one reservoir-sided port connected to a system fluid reservoir by a reservoir-sided pump conduit, said channel pump exhibiting a fluid backflow caused by a pressure difference in the tip- and reservoir-sided pump conduits resulting in an effective flow rate ($F_{\mathit{eff}}$) compared to a nominal flow rate ($F_{nom}$);
   determining a pressure difference ($\Delta p$) in said tip- and reservoir-sided pump conduits;
   based on said pressure difference ($\Delta p$), determining a volume difference ($\Delta V$) between a nominal volume ($V_{nom}$) and an effective volume ($V_{\mathit{eff}}$) pipetted by operating the channel pump during a pipetting period ($T_p$) at said nominal flow rate ($F_{nom}$), said effective volume ($V_{\mathit{eff}}$) being reduced compared to said nominal volume ($V_{nom}$) due to said fluid backflow;
   based on said determined volume difference ($\Delta V$), determining a period extension ($\Delta T$), the period extension ($\Delta T$) being adapted for pipetting said volume difference ($\Delta V$); and
   pipetting fluid by operating said channel pump at said nominal flow rate ($F_{nom}$) during an extended pipetting period ($T_{tot}$) which extends said pipetting period ($T_p$) by said period extension ($\Delta T$).

9. The method according to claim 8, further comprising measuring a fluid pressure in said tip-sided pump conduit, wherein said pressure difference ($\Delta p$) is determined based on the measured fluid pressure in the tip-sided pump conduit.

10. The method according to claim 8, further comprising determining a plurality of pressure differences ($\Delta p$) at different times, wherein determination of the extended pipetting period ($T_{tot}$) is based on the plural pressure differences.

11. The method according to claim 8, further comprising determining a fluid pressure in the tip-sided pump conduit by means of a calculation model, wherein said pressure difference ($\Delta p$) is determined based on the determined fluid pressure in the tip-sided pump conduit.

12. The method according to claim 8, further comprising transferring system fluid from said system fluid reservoir into an intermediate reservoir fluidically interconnected between said system fluid reservoir and said channel pump so as to have an invariant fluid level in said intermediate reservoir.

13. The method according to claim 12, wherein said pipetting tip is raised so that an orifice of said pipetting tip has a vertical position higher than said fluid level of said intermediate reservoir at least when said pipetting tip is moved towards or away from a pipetting position.

14. The method according to claim 12, wherein said pipetting tip is lowered so that said orifice has a vertical position lower than said fluid level of said intermediate reservoir during pipetting fluid at said pipetting position.

* * * * *